US006444875B1

(12) United States Patent
Dietrich

(10) Patent No.: US 6,444,875 B1
(45) **Date of Patent: *Sep. 3, 2002**

(54) IMIDAZOLINONE RESISTANT AHAS MUTANTS

(75) Inventor: Gabriele Elfriede Dietrich, Rocky Hill, NJ (US)

(73) Assignee: BASF Aktiengesellschaft, Ludwigshafen (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/096,562

(22) Filed: Jun. 12, 1998

Related U.S. Application Data

(63) Continuation of application No. 07/894,062, filed on Jun. 8, 1992, now Pat. No. 5,767,361, which is a continuation-in-part of application No. 07/737,851, filed on Jul. 31, 1991, now Pat. No. 5,731,180.

(51) Int. Cl.$^{7}$ .......................... A01H 5/00; C12N 5/04

(52) U.S. Cl. .......................... 800/279; 536/23.6

(58) Field of Search .......................... 800/320.1, 320, 800/260, 275; 536/23.6; 435/419, 430

(56) References Cited

U.S. PATENT DOCUMENTS 4,761,373 A * 8/1988 Anderson et al. ........ 435/172.3
5,731,180 A * 3/1998 Dietrich et al. .......... 435/172.3
5,767,361 A * 6/1998 Dietrich et al. ............. 800/205

FOREIGN PATENT DOCUMENTS

WO 92/08794 5/1992

OTHER PUBLICATIONS

Anderson et al., *Genome 31*:994–999, 1989.
Jen et al., *J. Cellular Biochem. 14E*(Supp.):302, Abstract, 1990.
Wiersma et al., *Mol. Gen. Genet. 219*:413–420, 1989.
Lesser, W.H., ed., *Animal Patents*, N.Y., Stockton Press, 1989, p. 159.
Haughn, G. et al., *Plant Physiology 92*:1081–1085, Apr. 1990.
Sathasivan et al., *Nucleic Acids Research 18*:2188, Apr. 1990.
Haughn, G. et al., *Mol. Gen. Genet. 211*:266–271, 1988.
Old, R.W. et al., *Principles of Genetic Manipulation*, 4$^{th}$ Ed., Oxford U.K. Blackwell Scientific Publ., 1989, pp. 87–98.
Lawther, R.P. et al., *Proc. Natl. Acad. Sci. USA 78*(2):922–925, Feb. 1981.
Burr, B. et al., *TIG 7*(2):55–61, 1991.
Lee, K.Y. et al., *The EMBO Journal 7*(5):1241–1248, 1988.
Falco, S.C. et al., *Genetics 109*:21–35, 1985.
Mazur, B.J. et al., *Plant Physiol. 85*:1110–1117, 1987.
Falco, S.C. et al., *Nucleic Acids Research 13*(11):4011–4027, 1985.
Klein, T.M. et al., *Nature 327*:70–73, May 1987.
Squires, C.H. et al., *Nucleic Acids Research 11*(15):5299–5313, 1983.

* cited by examiner

*Primary Examiner*—David T. Fox
*Assistant Examiner*—David H Kruse
(74) *Attorney, Agent, or Firm*—Anne Rosenblum

(57) ABSTRACT

The present invention relates to mutant AHAS enzymes that are specifically resistant to imidazolinone herbicides. Exemplary of these is a corn sequence, which encodes an amino acid substitution at position 621 of the wild-type AHAS enzyme. Polynucleotides encoding the mutant enzyme can be used in screening methods for identifying plant cells that have been transformed.

3 Claims, 29 Drawing Sheets

W22/1A and B73/7-4 sequence: 5'TAGTG3' 3'ATCTG5'

XII2/8A sequence: 5'TAATG3' 3'ATTAC5'

```
 40          50          60          70          80          90
  *           *           *           *           *           *
ATG GCC ACC GCC GCC GCC GCG TCT ACC GCG CTC ACT GGC GCC ACT ACC GCT GCG
Met Ala Thr Ala Ala Ala Ala Ser Thr Ala Leu Thr Gly Ala Thr Thr Ala Ala

        100         110         120         130         140
          *           *           *           *           *
CCC AAG GCG AGG CGC CGG GCG CAC CTC CTG GCC ACC CGC CGC GCC CTC GCC GCG
Pro Lys Ala Arg Arg Arg Ala His Leu Leu Ala Thr Arg Arg Ala Leu Ala Ala

   150         160         170         180         190
     *           *           *           *           *
CCC ATC AGG TGC TCA GCG GCG TCA CCC GCC ATG CCG ATG GCT CCC CCG GCC ACC
Pro Ile Arg Cys Ser Ala Ala Ser Pro Ala Met Pro Met Ala Pro Pro Ala Thr

200         210         220         230         240         250
*           *           *           *           *           *
CCG CTC CGG CCG TGG GGC CCC ACC GAT CCC CGC AAG GGC GCC GAC ATC CTC GTC
Pro Leu Arg Pro Trp Gly Pro Thr Asp Pro Arg Lys Gly Ala Asp Ile Leu Val

      260         270         280         290         300
        *           *           *           *           *
GAG TCC CTC GAG CGC TGC GGC GTC CGC GAC GTC TTC GCC TAC CCC GGC GGC GCG
Glu Ser Leu Glu Arg Cys Gly Val Arg Asp Val Phe Ala Tyr Pro Gly Gly Ala
```

FIG.6A

```
 310        320        330         340        350        360
   *          *          *           *          *          *
TCC ATG GAG ATC CAC CAG GCA CTC ACC CGC TCC CCC GTC ATC GCC AAC CAC CTC
Ser Met Glu Ile His Gln Ala Leu Thr Arg Ser Pro Val Ile Ala Asn His Leu

            370        380        390        400        410
              *          *          *          *          *
TTC CGC CAC GAG CAA GGG GAG GCC TTT GCG GCC TCC GGC TAC GCG CGC TCC TCG
Phe Arg His Glu Gln Gly Glu Ala Phe Ala Ala Ser Gly Tyr Ala Arg Ser Ser

    420         430        440        450         460
      *           *          *          *           *
GGC CGC GTC GGC GTC TGC ATC GCC ACC TCC GGC CCC GGC GCC ACC AAC CTT GTC
Gly Arg Val Gly Val Cys Ile Ala Thr Ser Gly Pro Gly Ala Thr Asn Leu Val

470        480         490        500        510         520
  *          *           *          *          *           *
TCC GCG CTC GCC GAC GCG CTG CTC GAT TCC GTC CCC ATG GTC GCC ATC ACG GGA
Ser Ala Leu Ala Asp Ala Leu Leu Asp Ser Val Pro Met Val Ala Ile Thr Gly
```

FIG.6B

```
      530         540         550         560         570
        *           *           *           *           *
CAG GTG CCG CGA CGC ATG ATT GGC ACC GAC GCC TTC CAG GAG ACG CCC ATC GTC
Gln Val Pro Arg Arg Met Ile Gly Thr Asp Ala Phe Gln Glu Thr Pro Ile Val

  580         590         600         610         620         630
    *           *           *           *           *           *
GAG GTC ACC CGC TCC ATC ACC AAG CAC AAC TAC CTG GTC CTC GAC GTC GAC GAC
Glu Val Thr Arg Ser Ile Thr Lys His Asn Tyr Leu Val Leu Asp Val Asp Asp

        640         650         660         670         680
          *           *           *           *           *
ATC CCC CGC GTC GTG CAG GAG GCT TTC TTC CTC GCC TCC TCT GGT CGA CCG GGG
Ile Pro Arg Val Val Gln Glu Ala Phe Phe Leu Ala Ser Ser Gly Arg Pro Gly

    690         700         710         720         730
      *           *           *           *           *
CCG GTG CTT GTC GAC ATC CCC AAG GAC ATC CAG CAG CAG ATG GCG GTG CCT GTC
Pro Val Leu Val Asp Ile Pro Lys Asp Ile Gln Gln Gln Met Ala Val Pro Val
```

FIG.6C

```
740                 750                 760                 770                 780                 790
 *                   *                   *                   *                   *                   *
TGG GAC AAG CCC ATG AGT CTG CCT GGG TAC ATT GCG CGC CTT CCC AAG CCC CCT
Trp Asp Lys Pro Met Ser Leu Pro Gly Tyr Ile Ala Arg Leu Pro Lys Pro Pro

        800                 810                 820                 830                 840
         *                   *                   *                   *                   *
GCG ACT GAG TTG CTT GAG CAG GTG CTG CGT CTT GTT GGT GAA TCC CGG CGC CCT
Ala Thr Glu Leu Leu Glu Gln Val Leu Arg Leu Val Gly Glu Ser Arg Arg Pro

  850                 860                 870                 880                 890                 900
   *                   *                   *                   *                   *                   *
GTT CTT TAT GTT GGC GGT GCG TGC GCA GCA TCT GGT GAG GAG TTG CGA CGC TTT
Val Leu Tyr Val Gly Gly Ala Cys Ala Ala Ser Gly Glu Glu Leu Arg Arg Phe

             910                 920                 930                 940                 950
              *                   *                   *                   *                   *
GTG GAG CTG ACT GGA ATC CCG GTC ACA ACT ACT CTT ATG GGC CTC GGC AAC TTC
Val Glu Leu Thr Gly Ile Pro Val Thr Thr Thr Leu Met Gly Leu Gly Asn Phe
```

FIG.6D

```
     960          970        980        990        1000
       *            *          *          *           *
CCC AGC GAC GAC CCA CTG TCT CTG CGC ATG CTA GGT ATG CAT GGC ACG GTG TAT
Pro Ser Asp Asp Pro Leu Ser Leu Arg Met Leu Gly Met His Gly Thr Val Tyr

1010       1020        1030       1040       1050        1060
  *          *           *          *          *           *
GCA AAT TAT GCA GTG GAT AAG GCC GAT CTG TTG CTT GCA CTT GGT GTG CGG TTT
Ala Asn Tyr Ala Val Asp Lys Ala Asp Leu Leu Leu Ala Leu Gly Val Arg Phe

       1070       1080        1090       1100       1110
         *          *           *          *          *
GAT GAT CGT GTG ACA GGG AAG ATT GAG GCT TTT GCA AGC AGG GCT AAG ATT GTG
Asp Asp Arg Val Thr Gly Lys Ile Glu Ala Phe Ala Ser Arg Ala Lys Ile Val

  1120       1130       1140        1150       1160       1170
     *          *          *           *          *          *
CAC GTT GAT ATT GAT CCG GCT GAG ATT GGC AAG AAC AAG CAG CCA CAT GTG TCC
His Val Asp Ile Asp Pro Ala Glu Ile Gly Lys Asn Lys Gln Pro His Val Ser
```

FIG.6E

```
          1180        1190        1200         1210        1220
             *           *           *            *           *
ATC TGT GCA GAT GTT AAG CTT GCT TTG CAG GGC ATG AAT GCT CTT CTT GAA GGA
Ile Cys Ala Asp Val Lys Leu Ala Leu Gln Gly Met Asn Ala Leu Leu Glu Gly

    1230        1240        1250        1260        1270
       *           *           *           *           *
AGC ACA TCA AAG AAG AGC TTT GAC TTT GGC TCA TGG AAC GAT GAG TTG GAT CAG
Ser Thr Ser Lys Lys Ser Phe Asp Phe Gly Ser Trp Asn Asp Glu Leu Asp Gln

1280       1290        1300        1310        1320        1330
   *          *           *           *           *           *
CAG AAG AGG GAA TTC CCC CTT GGG TAT AAA ACA TCT AAT GAG GAG ATC CAG CCA
Gln Lys Arg Glu Phe Pro Leu Gly Tyr Lys Thr Ser Asn Glu Glu Ile Gln Pro

      1340        1350        1360        1370        1380
         *           *           *           *           *
CAA TAT GCT ATT CAG GTT CTT GAT GAG CTG ACG AAA GGC GAG GCC ATC ATC GGC
Gln Tyr Ala Ile Gln Val Leu Asp Glu Leu Thr Lys Gly Glu Ala Ile Ile Gly
```

FIG.6F

```
1390          1400          1410           1420          1430          1440
   *             *             *              *             *             *
ACA GGT GTT GGG CAG CAC CAG ATG TGG GCG GCA CAG TAC TAC ACT TAC AAG CGG
Thr Gly Val Gly Gln His Gln Met Trp Ala Ala Gln Tyr Tyr Thr Tyr Lys Arg

         1450          1460          1470           1480          1490
            *             *             *              *             *
CCA AGG CAG TGG TTG TCT TCA GCT GGT CTT GGG GCT ATG GGA TTT GGT TTG CCG
Pro Arg Gln Trp Leu Ser Ser Ala Gly Leu Gly Ala Met Gly Phe Gly Leu Pro

   1500           1510          1520          1530           1540
      *              *             *             *              *
GCT GCT GCT GGT GCT TCT GTG GCC AAC CCA GGT GTT ACT GTT GTT GAC ATC GAT
Ala Ala Ala Gly Ala Ser Val Ala Asn Pro Gly Val Thr Val Val Asp Ile Asp

1550          1560           1570          1580          1590           1600
  *             *              *             *             *              *
GGA GAT GGT AGC TTT CTC ATG AAC GTT CAG GAG CTA GCT ATG ATC CGA ATT GAG
Gly Asp Gly Ser Phe Leu Met Asn Val Gln Glu Leu Ala Met Ile Arg Ile Glu
```

FIG.6G

```
     1610      1620        1630      1640      1650
        *         *           *         *         *
AAC CTC CCG GTG AAG GTC TTT GTG CTA AAC AAC CAG CAC CTG GGG ATG GTG GTG
Asn Leu Pro Val Lys Val Phe Val Leu Asn Asn Gln His Leu Gly Met Val Val

 1660      1670      1680        1690      1700      1710
    *         *         *           *         *         *
CAG TGG GAG GAC AGG TTC TAT AAG GCC AAC AGA GCG CAC ACA TAC TTG GGA AAC
Gln Trp Glu Asp Arg Phe Tyr Lys Ala Asn Arg Ala His Thr Tyr Leu Gly Asn

       1720      1730      1740        1750      1760
          *         *         *           *         *
CCA GAG AAT GAA AGT GAG ATA TAT CCA GAT TTC GTG ACG ATC GCC AAA GGG TTC
Pro Glu Asn Glu Ser Glu Ile Tyr Pro Asp Phe Val Thr Ile Ala Lys Gly Phe

  1770        1780      1790      1800        1810
     *           *         *         *           *
AAC ATT CCA GCG GTC CGT GTG ACA AAG AAG AAC GAA GTC CGC GCA GCG ATA AAG
Asn Ile Pro Ala Val Arg Val Thr Lys Asn Glu Val Arg Ala Ala Ile Lys
```

FIG.6H

```
1820          1830          1840          1850          1860          1870
  *             *             *             *             *             *
AAG ATG CTC GAG ACT CCA GGG CCG TAC CTC TTG GAT ATA ATC GTC CCA CAC CAG
Lys Met Leu Glu Thr Pro Gly Pro Tyr Leu Leu Asp Ile Ile Val Pro His Gln

        1880          1890          1900          1910          1920
          *             *             *             *             *
GAG CAT GTG TTG CCT ATG ATC CCT AAT GGT GGG GCT TTC AAG GAT ATG ATC CTG
Glu His Val Leu Pro Met Ile Pro Asn Gly Gly Ala Phe Lys Asp Met Ile Leu

   1930          1940          1950          1960
      *             *             *             *
GAT GGT GAT GGC AGG ACT GTG TAC TGATC TAAAA TCCAG CAAG
Asp Gly Asp Gly Arg Thr Val Tyr
```

FIG. 6I

```
                    10          20          30          40          50
         AACCC TCGCG CCGCC TCCGA GACAG CCGCC GCAAC CATGG CCACC GCCGC CGCCG CGTCT

         AACCC TCGCG CCGCC TCCGA GACAG CCGCC GCAAC CATGG CCACC GCCGC CGCCG CGTCT
         11111 11111 11111 11111 11111 11111 11111 11111 11111 11111 11111 11111
B73/7-4  AACCC TCGCG CCGCC TCCGA GACAG CCGCC GCAAC CATGG CCACC GCCGC CGCCG CGTCT
         11111 11111 11111 11111 11111 11111 11111 11111 11111 11111 11111 11111
XI12/8A  AACCC TCGCG CCGCC TCCGA GACAG CCGCC GCAAC CATGG CCACC GCCGC CGCCG CGTCT

                    70          80          90         100         110         120
XI12/8A  ACCGC GCTCA CTGGC GCCAC TACCG CTGCG CCCAA GGCGA GGCGC CGGGC GCACC TCCTG

W22/1A   ACCGC GCTCA CTGGC GCCAC TACCG CTGCG CCCAA GGCGA GGCGC CGGGC GCACC TCCTG
         11111 11111 11111 11111 11111 11111 11111 11111 11111 11111 11111 11111
B73/7-4  ACCGC GCTCA CTGGC GCCAC TACCG CTGCG CCCAA GGCGA GGCGC CGGGC GCACC TCCTG
         11111 11111 11111 11111 11111 11111 11111 11111 11111 11111 11111 11111
XI12/8A  ACCGC GCTCA CTGGC       TACCG CTGCG CCCAA GGCGA GGCGC CGGGC GCACC TCCTG

                   130         140         150         160         170         180
XI12/8A  GCCAC CCGCC GCGCC CTCGC CGCGC CCATC AGGTG CTCAG CGGCG TCACC CGCCA TGCCG

W22/1A   GCCAC CCGCC GCGCC CTCGC CGCGC CCATC AGGTG CTCAG CGGCG TCACC CGCCA TGCCG
         11111 11111 11111 11111 11111 11111 11111 11111 11111 11111 11111 11111
B73/7-4  GCCAC CCGCC GCGCC CTCGC CGCGC CCATC AGGTG CTCAG CGGCG TCACC CGCCA TGCCG
         11111 11111 11111 11111 11111 11111 11111 11111 11111 11111 11111 11111
         GCCAC CCGCC GCGCC CTCGC CGCGC CCATC AGGTG CTCAG CGGCG TCACC CGCCA TGCCG
```

FIG. 7A

```
                    190         200         210         220         230         240
XI12/8A  ATGGC TCCCC CGGCC ACCCC GCTCC GGCCG TGGGG CCCCA CCGAT CCCCG CAAGG GCGCC

W22/1A   ATGGC TCCCC CGGCC ACCCC GCTCC GGCCG TGGGG CCCCA CCGAT CCCCG CAAGG GCGCC
         11111 11111 11111 11111 11111 11111 11111 11111 11111 11111 11111 11111
B73/7-4  ATGGC TCCCC CGGCC                                                 GtGCt
         11111 11111 11111 11111 11111 11111 11111 11111 11111 11111 11111 11111
XI12/8A  ATGGC TCCCC CGGCC ACCCC GCTCC GGCCG TGGGG CCCCA CCGAT CCCCG CAAGG GCGCC

                    250         260         270         280         290         300
XI12/8A  GACAT CCTCG TCGAG TCCCT CGAGC GCTGC GGCGT CCGCG ACGTC TTCGC CTACC CCGGC

W22/1A   GACAT CCTCG TCGAG TCCCT CGAGC GCTGC GGCGT CCGCG ACGTC TTCGC CTACC CCGGC
         11111 11111 11111 11111 11111 11111 11111 11111 11111 11111 11111 11111
B73/7-4  GACAT CCTCG TCGAG TCCCT CGAGC GCTGC GGCGT CCGCG ACGTC TTCGC CTACC CCGGC
         11111 11111 11111 11111 11111 11111 11111 11111 11111 11111 11111 11111
XI12/8A  GACAT CCTCG TCGAG TCCCT CGAGC GCTGC GGCGT CCGCG ACGTC TTCGC CTACC CCGGC

                    310         320         330         340         350         360
XI12/8A  GGCGC GTCCA TGGAG ATCCA CCAGG CACTC ACCCG CTCCC CCGTC ATCGC CAACC ACCTC

W22/1A   GGCGC GTCCA TGGAG ATCCA CCAGG CACTC ACCCG CTCCC CCGTC ATCGC CAACC ACCTC
         11111 11111 11111 11111 11111 11111 11111 11111 11111 11111 11111 11111
XB73/7-4 GGCGC GTCCA TGGAG ATCCA CCAGG CACTC ACCCG CTCCC CCGTC ATCGC CAACC ACCTC
         11111 11111 11111 11111 11111 11111 11111 11111 11111 11111 11111 11111
XI12/8A  GGCGC GTCCA TGGAG ATCCA CCAGG CACTC ACCCG CTCCC CCGTC ATCGC CAACC ACCTC
```

FIG. 7B

```
                  370         380         390         400         410         420
XI12/8A  TTCCG CCACG AGCAA GGGGA GGCCT TTGCG GCCTC CGGCT ACGCG CGCTC CTCGG GCCGC

W22/1A   TTCCG CCACG AGCAA GGGGA GGCCT TTGCG GCCTC CGGCT ACGCG CGCTC CTCGG GCCGC
         11111 11111 11111 11111 11111 11111 11111 11111 11111 11111 11111 11111
B73/7-4  TTCCG CCACG AGCAA GGGGA GGCCT       GCCTC CGGCT ACGCG CGCTC CTCGG GCCGC
         11111 11111 11111 11111 11111 11111 11111 11111 11111 11111 11111 11111
XI12/8A  TTCCG CCACG AGCAA GGGGA GGCCT TTGCG GCCTC CGGCT ACGCG CGCTC CTCGG GCCGC

                  430         440         450         460         470         480
XI12/8A  GTCGG CGTCT GCATC GCCAC CTCCG GCCCC GGCGC CACCA ACCTT GTCTC       TCGCC

W22/1A   GTCGG CGTCT GCATC GCCAC CTCCG GCCCC GGCGC CACCA ACCTT GTCTC CGCGC TCGCC
         11111 11111 11111 11111 11111 11111 11111 11111 11111 11111 11111 11111
B73/7-4  GTCGG CGTCT GCATC GCCAC CTCCG GCCCC GGCGC CACCA ACCTT GTCTC CGCGC TCGCC
         11111 11111 11111 11111 11111 11111 11111 11111 11111 11111 11111 11111
XI12/8A  GTCGG CGTCT GCATC GCCAC CTCCG GCCCC GGCGC CACCA ACCTT GTCTC       TCGCC

                  490         500         510         520         530         540
XI12/8A  GACGC GCTGC TCGAT TCCGT CCCCA TGGTC GCCAT CACGG GACAG GTGCC GCGAC GCATG

W22/1A   GACGC GCTGC TCGAT TCCGT CCCCA TGGTC GCCAT CACGG GACAG GTGCC GCGAC GCATG
         11111 11111 11111 11111 11111 11111 11111 11111 11111 11111 11111 11111
B73/7-4  GACGC GCTGC TCGAT TCCGT CCCCA TGGTC GCCAT CACGG GACAG GTGCC GCGAC GCATG
         11111 11111 11111 11111 11111 11111 11111 11111 11111 11111 11111 11111
XI12/8A  GACGC GCTGC TCGAT TCCGT CCCCA TGGTC GCCAT CACGG GACAG GTGCC GCGAC GCATG
```

FIG.7C

```
                550         560         570         580         590         600
XI12/8A   ATTGG CACCG ACGCC TTCCA GGAGA CGCCC ATCGT CGAGG TCACC CGCTC CATCA CCAAG

W22/1A    ATTGG CACCG ACGCC TTCCA GGAGA CGCCC ATCGT CGAGG TCACC CGCTC CATCA CCAAG
          11111 11111 11111 11111 11111 11111 11111 11111 11111 11111 11111 11111
B73/7-4   ATTGG CACCG ACGCC TTCCA GGAGA CGCCC ATCGT CGAGG TCACC CGCTC CATCA CCAAG
          11111 11111 11111 11111 11111 11111 11111 11111 11111 11111 11111 11111
XI12/8A   ATTGG CACCG ACGCC TTCCA GGAGA CGCCC ATCGT CGAGG TCACC CGCTC CATCA CCAAG

                610         620         630         640         650         660
XI12/8A   CACAA CTACC TGGTC CTCGA CGTCG ACGAC ATCCC CCGCG TCGTG CAGGA GGCTT TCTTC

W22/1A    CACAA CTACC TGGTC CTCGA CGTCG ACGAC ATCCC CCGCG TCGTG CAGGA GGCTT TCTTC
          11111 11111 11111 11111 11111 11111 11111 11111 11111 11111 11111 11111
B73/7-4         CTACC TGGTC CTCGA CGTCG ACGAC ATCCC CCGCG TCGTG CAGGA GGCTT TCTTC
          11111 11111 11111 11111 11111 11111 11111 11111 11111 11111 11111 11111
XI12/8A   CACAA CTACC TGGTC CTCGA CGTCG ACGAC ATCCC CCGCG TCGTG CAGGA GGCTT TCTTC

                670         680         690         700         710         720
XI12/8A   CTCGC CTCCT CTGGT CGACC GGGGC CGGTG CTTGT CGACA TCCCC AAGGA CATCC AGCAG

W22/1A    CTCGC CTCCT CTGGT CGACC GGGGC CGGTG CTTGT CGACA TCCCC AAGGA CATCC AGCAG
          11111 11111 11111 11111 11111 11111 11111 11111 11111 11111 11111 11111
B73/7-4   CTCGC CTCCT CTGGT CGACC       CGGTG CTTGT CGACA TCCCC AAGGA CATCC AGCAG
          11111 11111 11111 11111 11111 11111 11111 11111 11111 11111 11111 11111
XI12/8A   CTCGC CTCCT CTGGT CGACC GGGGC CGGTG CTTGT CGACA TCCCC AAGGA CATCC AGCAG
```

FIG.7D

```
                 730        740        750        760        770        780
XI12/8A   CAGAT GGCGG TGCCT GTCTG GGACA AGCCC ATGAG TCTGC CTGGG TACAT TGCGC GCCTT

W22/1A    CAGAT GGCGG TGCCT GTCTG GGACA AGCCC ATGAG TCTGC CTGGG TACAT TGCGC GCCTT
          11111 11111 11111 11111 11111 11111 11111 11111 11111 11111 11111 11111
B73/7-4   CAGAT GGCGG TGCCT GTCTG GGACA AGCCC ATGAG TCTGC CTGGG TACAT TGCGC GCCTT
          11111 11111 11111 11111 11111 11111 11111 11111 11111 11111 11111 11111
XI12/8A   CAGAT GGCGG TGCCT GTCTG GGACA AGCCC ATGAG TCTGC CTGGG TACAT TGCGC GCCTT

                 790        800        810        820        830        840
XI12/8A   CCCAA GCCCC CTGCG ACTGA GTTGC TTGAG CAGGT GCTGC       GTTGG TGAAT CCCGG

W22/1A    CCCAA GCCCC CTGCG ACTGA GTTGC TTGAG CAGGT GCTGC       GTTGG TGAAT CCCGG
          11111 11111 11111 11111 11111 11111 11111 11111 11111 11111 11111 11111
B73/7-4   CCCAA GCCCC CTGCG ACTGA GTTGC TTGAG CAGGT GCTGC       GTTGG TGAAT CgCGG
          11111 11111 11111 11111 11111 11111 11111 11111 11111 11111 11111 11111
XI12/8A   CCCAA GCCCC CTGCG ACTGA GTTGC TTGAG CAGGT GCTGC       GTTGG TGAAT CCCGG

                 850        860        870        880        890        900
XI12/8A   CGCCC TGTTC TTTAT GTTGG CGGTG CGTGC GCAGC ATCTG GTGAG GAGTT GCGAC GCTTT

W22/1A    CGCCC TGTTC TTTAT GTTGG CGGTG       GCAGC ATCTG GTGAG GAGTT GCGAC GCTTT
          11111 11111 11111 11111 11111 11111 11111 11111 11111 11111 11111 11111
B73/7-4   CGCCC TGTTC TTTAT       CGGTG       GCAGC ATCTG GTGAG GAGTT GCGAC GCTTT
          11111 11111 11111 11111 11111 11111 11111 11111 11111 11111 11111 11111
XI12/8A   CGCCC TGTTC TTTAT GTTGG CGGTG       GCAGC ATCTG GTGAG GAGTT GCGAC GCTTT
```

FIG. 7E

```
                  910         920         930         940         950         960
XI12/8A   GTGGA GCTGA CTGGA ATCCC GGTCA CAACT ACTCT TATGG GCCTC GGCAA CTTCC CCAGC

W22/1A    GTGGA GCTGA CTGGA ATCCC GGTCA CAACT ACTCT TATGG GCCTC GGCAA CTTCC CCAGC
          11111 11111 11111 11111 11111 11111 11111 11111 11111 11111 11111 11111
B73/7-4   GTGGA GCTGA CTGGA ATCCC GGTCA CAACT ACTCT TATGG GCCTC GGCAA CTTCC CCAGC
          11111 11111 11111 11111 11111 11111 11111 11111 11111 11111 11111 11111
XI12/8A   GTGGA GCTGA CTGGA ATCCC GGTCA CAACT ACTCT TATGG GCCTC GGCAA CTTCC CCAGC

                  970         980         990        1000        1010        1020
XI12/8A   GACGA CCCAC TGTCT CTGCG CATGC TAGGT ATGCA TGGCA CGGTG TATGC AAATT ATGCA

W22/1A    GACGA CCCAC TGTCT CTGCG CATGC TAGGT ATGCA TGGCA CGGTG TATGC AAATT ATGCA
          11111 11111 11111 11111 11111 11111 11111 11111 11111 11111 11111 11111
B73/7-4   GACGA CCCAC TGTCT CTGCG CATGC TAGGT ATGCA       CGGTG TATGC AAATT ATGCA
          11111 11111 11111 11111 11111 11111 11111 11111 11111 11111 11111 11111
XI12/8A   GACGA CCCAC TGTCT CTGCG CATGC TAGGT ATGCA TGGCA CGGTG TATGC AAATT ATGCA

                 1030        1040        1050        1060        1070        1080
XI12/8A   GTGGA TAAGG CCGAT CTGTT GCTTG CACTT GGTGT GCGGT TTGAT GATCG TGTGA CAGGG

W22/1A    GTGGA TAAGG CCGAT CTGTT GCTTG CACTT GGTGT GCGGT TTGAT GATCG TGTGA CAGGG
          11111 11111 11111 11111 11111 11111 11111 11111 11111 11111 11111 11111
B73/7-4   GTGGA TAAGG CCGAT CTGTT GCTTG CACTT GGTGT GCGGT TTGAT GATCG       CAGGG
          11111 11111 11111 11111 11111 11111 11111 11111 11111 11111 11111 11111
XI12/8A   GTGGA TAAGG CCGAT CTGTT GCTTG CACTT GGTGT GCGGT TTGAT GATCG TGTGA CAGGG
```

FIG.7F

```
                 1090       1100       1110       1120       1130       1140
XI12/8A   AAGAT TGAGG CTTTT GCAAG CAGGG CTAAG ATTGT GCACG TTGAT ATTGA TCCGG CTGAG

W22/1A    AAGAT TGAGG CTTTT GCAAG CAGGG CTAAG ATTGT GCACG TTGAT ATTGA TCCGG CTGAG
          11111 11111 11111 11111 11111 11111 11111 11111 11111 11111 11111 11111
B73/7-4   AAGAT TGAGG CTTTT GCAAG CAGGG CTAAG ATTGT GCACG TTGAT ATTGA TCCGG CTGAG
          11111 11111 11111 11111 11111 11111 11111 11111 11111 11111 11111 11111
XI12/8A   AAGAT TGAGG CTTTT GCAAG CAGGG CTAAG ATTGT GCACG TTGAT ATTGA TCCGG CTGAG

                 1150       1160       1170       1180       1190       1200
XI12/8A   ATTGG CAAGA ACAAG CAGCC ACATG TGTCC ATCTG TGCAG ATGTT AAGCT TGCTT TGCAG

W22/1A    ATTGG CAAGA ACAAG CAGCC ACATG TGTCC ATCTG TGCAG ATGTT AAGCT TGCTT TGCAG
          11111 11111 11111 11111 11111 11111 11111 11111 11111 11111 11111 11111
B73/7-4   ATTGG CAAGA ACAAG CAGCC ACATG TGTCC ATCTG TGCAG ATGTT AAGCT TGCTT TGCAG
          11111 11111 11111 11111 11111 11111 11111 11111 11111 11111 11111 11111
XI12/8A   ATTGG CAAGA ACAAG CAGCC ACATG TGTCC ATCTG TGCAG ATGTT AAGCT TGCTT TGCAG

                 1210       1220       1230       1240       1250       1260
XI12/8A   GGCAT GAATG CTCTT CTTGA AGGAA GCACA TCAAA GAAGA GCTTT GACTT TGGCT CATGG

W22/1A    GGCAT GAATG CTCTT CTTGA AGGAA GCACA TCAAA GAAGA GCTTT GACTT TGGCT CATGG
          11111 11111 11111 11111 11111 11111 11111 11111 11111 11111 11111 11111
B73/7-4   GGCAT GAATG CTCTT CTTGA AGGAA GCACA TCAAA GAAGA GCTTT GACTT TGGCT CATGG
          11111 11111 11111 11111 11111 11111 11111 11111 11111 11111 11111 11111
XI12/8A   GGCAT GAATG CTCTT CTTGA AGGAA GCACA TCAAA GAAGA GCTTT GACTT TGGCT CATGG
```

FIG. 7G

```
                1270        1280        1290        1300        1310        1320
XI12/8A   AACGA TGAGT TGGAT CAGCA GAAGA GGGAA TTCCC CCTTG GGTAT AAAAC ATCTA ATGAG

W22/1A    AACGA TGAGT TGGAT CAGCA GAAGA GGGAA TTCCC CCTTG GGTAT AAAAC ATCTA ATGAG
          11111 11111 11111 11111 11111 11111 11111 11111 11111 11111 11111 11111
B73/7-4   AACGA TGAGT TGGAT CAGCA GAAGA GGGAA TTCCC CCTTG GGTAT AAAAC ATCTA ATGAG
          11111 11111 11111 11111 11111 11111 11111 11111 11111 11111 11111 11111
XI12/8A   AACGA TGAGT TGGAT CAGCA GAAGA GGGAA TTCCC CCTTG GGTAT AAAAC ATCTA ATGAG

                1330        1340        1350        1360        1370        1380
XI12/8A   GAGAT CCAGC CACAA TATGC TATTC AGGTT CTTGA TGAGC TGACG AAAGG CGAGG CCATC

W22/1A    GAGAT CCAGC CACAA TATGC TATTC AGGTT CTTGA TGAGC TGACG AAAGG CGAGG CCATC
          11111 11111 11111 11111 11111 11111 11111 11111 11111 11111 11111 11111
B73/7-4   GAGAT CCAGC CACAA TATGC TATTC AGGTT CTTGA TGAGC TGACG AAAGG CGAGG CCATC
          11111 11111 11111 11111 11111 11111 11111 11111 11111 11111 11111 11111
XI12/8A   GAGAT CCAGC CACAA TATGC TATTC AGGTT CTTGA TGAGC TGACG AAAGG CGAGG CCATC

                1390        1400        1410        1420        1430        1440
          ATCGG CACAG GTGTT GGGCA GCACC AGATG TGGGC GGCAC AGTAC TACAC TTACA AGCGG

W22/1A    ATCGG CACAG GTGTT GGGCA GCACC AGATG TGGGC GGCAC AGTAC TACAC TTACA AGCGG
          11111 11111 11111 11111 11111 11111 11111 11111 11111 11111 11111 11111
B73/7-4   ATCGG CACAG GTGTT GGGCA GCACC AGATG TGGGC GGCAC AGTAC TACAC TTACA AGCGG
          11111 11111 11111 11111 11111 11111 11111 11111 11111 11111 11111 11111
XI12/8A   ATCGG CACAG GTGTT GGGCA GCACC AGATG TGGGC GGCAC AGTAC TACAC TTACA AGCGG
```

FIG. 7H

```
                  1450        1460        1470        1480        1490        1500
XI12/8A    CCAAG GCAGT GGTTG TCTTC AGCTG GTCTT GGGGC TATGG GATTT GGTTT GCCGG CTGCT

W22/1A     CCAAG GCAGT GGTTG TCTTC AGCTG GTCTT GGGGC TATGG GATTT GGTTT GCCGG CTGCT
           11111 11111 11111 11111 11111 11111 11111 11111 11111 11111 11111 11111
B73/7-4    CCAAG GCAGT GGTTG TCTTC AGCTG GTCTT GGGGC TATGG GATTT GGTTT GCCGG CTGCT
           11111 11111 11111 11111 11111 11111 11111 11111 11111 11111 11111 11111
XI12/8A    CCAAG GCAGT GGTTG TCTTC AGCTG GTCTT GGGGC TATGG GATTT GGTTT GCCGG CTGCT

                  1510        1520        1530        1540        1550        1560
XI12/8A    GCTGG TGCTT CTGTG GCCAA CCCAG GTGTT ACTGT TGTTG ACATC GATGG AGATG GTAGC
                                            >
W22/1A     GCTGG TGCTT CTGTG GCaAA CCCAG GTGTT ACTGT TGTTG ACATC GATGG AGATG GTAGC
           11111 11111 11111 11111 11111 1111  11111 11111 11111 11111 11111 11111
B73/7-4    GCTGG TGCTT CTGTG GCaAA CCCAG GTGTc ACTGT TGTTG ACATC GATGG AGATG GTAGC
           11111 11111 11111 11 11 11111 1111  11111 11111 11111 11111 11111 11111
XI12/8A    GCTGG TGCTT CTGTG GCCAA CCCAG GTGTT ACTGT TGTTG ACATC GATGG AGATG GTAGC

                  1570        1580        1590        1600        1610        1620
XI12/8A    TTTCT CATGA ACGTT CAGGA GCTAG CTATG ATCCG AATTG AGAAC CTCCC GGTGA AGGTC
                                                                      >
W22/1A     TTTCT CATGA ACGTT CAGGA GCTAG CTATG ATCCG AATTG AGAAC CTCCC GGTGA AGGTC
           11111 11111 11111 11111 11111 11111 11111 11111 11111 11111 1111  11111
B73/7-4    TTTCT CATGA ACGTT CAGGA GCTAG CTATG ATCCG AATTG AGAAC CTCCC aGTGA AGGTC
           11111 11111 11111 11111 11111 11111 11111 11111 11111 11111 1111  11111
XI12/8A    TTTCT CATGA ACGTT CAGGA GCTAG CTATG ATCCG AATTG AGAAC CTCCC GGTGA AGGTC
```

FIG.7I

```
                 1630        1640        1650        1660        1670        1680
XI12/8A   TTTGT GCTAA ACAAC CAGCA CCTGG GGATG GTGGT GCAGT GGGAG GACAG GTTCT ATAAG
                                                        #
W22/1A    TTTGT GCTAA ACAAC CAGCA CCTGG GGATG GTGGT GCAGT GGGAG GACAG GTTCT ATAAG
          11111 11111 11111 11111 11111 11111 11111 11111 1111  11111 11111 11111
B73/7-4   TTTGT GCTAA ACAAC CAGCA CCTGG GGATG GTGGT GCAGT tGGAG GACAG GTTCT ATAAG
          11111 11111 11111 11111 11111 11111 11111 11111 1111  11111 11111 11111
XI12/8A   TTTGT GCTAA ACAAC CAGCA CCTGG GGATG GTGGT GCAGT GGGAG GACAG GTTCT ATAAG

                 1690        1700        1710        1720        1730        1740
XI12/8A   GCCAA CAGAG CGCAC ACATA CTTGG GAAAC CCAGA GAATG AAAGT GAGAT ATATC CAGAT

W22/1A    GCCAA CAGAG CGCAC ACATA CTTGG GAAAC CCAGA GAATG AAAGT GAGAT ATATC CAGAT
          11111 11111 11111 11111 11111 11111 11111 11111 11111 11111 11111 11111
B73/7-4   GCCAA CAGAG CGCAC ACATA CTTGG GAAAC CCAGA GAATG AAAGT GAGAT ATATC CAGAT
          11111 11111 11111 11111 11111 11111 11111 11111 11111 11111 11111 11111
XI12/8A   GCCAA CAGAG CGCAC ACATA CTTGG GAAAC CCAGA GAATG AAAGT GAGAT ATATC CAGAT

                 1750        1760        1770        1780        1790        1800
XI12/8A   TTCGT GACGA TCGCC AAAGG GTTCA ACATT CCAGC GGTCC GTGTG ACAAA GAAGA ACGAA

W22/1A    TTCGT GACGA TCGCC AAAGG GTTCA ACATT CCAGC GGTCC GTGTG ACAAA GAAGA ACGAA
          11111 11111 11111 11111 11111 11111 11111 11111 11111 11111 11111 11111
B73/7-4   TTCGT GACGA TCGCC AAAGG GTTCA ACATT CCAGC GGTCC GTGTG ACAAA GAAGA ACGAA
          11111 11111 11111 11111 11111 11111 11111 11111 11111 11111 11111 11111
XI12/8A   TTCGT GACGA TCGCC AAAGG GTTCA ACATT CCAGC GGTCC GTGTG ACAAA GAAGA ACGAA
```

FIG.7J

```
                  1810       1820       1830       1840       1850       1860
XI12/8A  GTCCG CGCAG CGATA AAGAA GATGC TCGAG ACTCC AGGGC CGTAC CTCTT GGATA TAATC

W22/1A   GTCCG CGCAG CGATA AAGAA GATGC TCGAG ACTCC AGGGC CGTAC CTCTT GGATA TAATC
         11111 11111 11111 11111 11111 11111 11111 11111 11111 11111 11111 11111
B73/7-4  GTCCG CGCAG CGATA AAGAA GATGC TCGAG ACTCC AGGGC CGTAC CTCTT GGATA TAATC
         11111 11111 11111 11111 11111 11111 11111 11111 11111 11111 11111 11111
XI12/8A  GTCCG CGCAG CGATA AAGAA GATGC TCGAG ACTCC AGGGC CGTAC CTCTT GGATA TAATC

                  1870       1880       1890       1900       1910       1920
XI12/8A  GTCCC ACACC AGGAG CATGT GTTGC CTATG ATCCC TAATG GTGGG GCTTT CAAGG ATATG

W22/1A   GTCCC ACACC AGGAG CATGT GTTGC CTATG ATCCC TAgTG GTGGG GCTTT CAAGG ATATG
         11111 11111 11111 11111 11111 11111 11111 11111 11111 11111 11111 11111
B73/7-4  GTCCC ACACC AGGAG CATGT GTTGC CTATG ATCCC TAgTG GTGGG GCTTT CAAGG ATATG
         11111 11111 11111 11111 11111 11111 11111 11 11 11111 11111 11111 11111
XI12/8A  GTCCC ACACC AGGAG CATGT GTTGC CTATG ATCCC TAATG GTGGG GCTTT CAAGG ATATG

                  1930       1940       1950       1960
XI12/8A  ATCTT GGATG GTGAT GGCAG GACTG TGTAC TGATC TAAAA TCCAG CAAG

W22/1A   ATCTT GGATG GTGAT GGCAG GACTG TGTAC TGATC TAAAA TCCAG CAAG>
         11111 11111 11111 11111 11111 11111 11111 11111 11111 1111
B73/7-4  ATCTT GGATG GTGAT GGCAG GACTG TGTAC TGATC TAAAA TCCAG CAAG>
         11111 11111 11111 11111 11111 11111 11111 11111 11111 1111
XI12/8A  ATCTT GGATG GTGAT GGCAG GACTG TGTAC TGATC TAAAA TCCAG CAAG
```

FIG. 7K

```
                    10         20         30         40         50         60
XI12/8A   MATAA AASTA LTGAT TAAPK ARRRA HLLAT RRALA APIRC SAASP AMPMA PPATP LRPWG

W22/1A    MATAA AASTA LTGAT TAAPK ARRRA HLLAT RRALA APIRC SAASP AMPMA PPATP LRPWG
          11111 11111 111 1 11111 11111 11111 11111 11111 11111 11111 11111 11111
B73/7-4   MATAA AASTA LTGAT TAAPK ARRRA HLLAT RRALA APIRC SAASP AMPMA PPATP LRPWG
          11111 11111 11111 11111 11111 11111 11111 11111 11111 11111 11111 11111
XI12/8A   MATAA AASTA LTGAT TAAPK ARRRA HLLAT RRALA APIRC SAASP AMPMA PPATP LRPWG

                    70         80         90        100        110        120
XI12/8A   PTDPR KGADI LVESL ERCGV RDVFA YPGGA SMEIH QALTR SPVIA NHLFR HEQGE AFAAS
            #
W22/1A    PTDPR KGADI LVESL ERCGV RDVFA YPGGA SMEIH QALTR SPVIA NHLFR HEQGE AFAAS
          11 11 11111 11111 11111 11111 11111 11111 11111 11111 11111 11111 11111
B73/7-4   PTePR KGADI LVESL ERCGV RDVFA YPGGA SMEIH QALTR SPVIA NHLFR HEQGE AFAAS
          11 11 11111 11111 11111 11111 11111 11111 11111 11111 11111 11111 11111
XI12/8A   PTDPR KGADI LVESL ERCGV RDVFA YPGGA SMEIH QALTR SPVIA NHLFR HEQGE AFAAS

                   130        140        150        160        170        180
XI12/8A   GYARS SGRVG VCIAT SGPGA TNLVS ALADA LLDSV PMVAI TGQVP RRMIG TDAFQ ETPIV

W22/1A    GYARS SGRVG VCIAT SGPGA TNLVS ALADA LLDSV PMVAI TGQVP RRMIG TDAFQ ETPIV
          11111 11111 11111 11111 11111 11111 11111 11111 11111 11111 11111 11111
B73/7-4   GYARS SGRVG VCIAT SGPGA TNLVS ALADA LLDSV PMVAI TGQVP RRMIG TDAFQ ETPIV
          11111 11111 11111 11111 11111 11111 11111 11111 11111 11111 11111 11111
XI12/8A   GYARS SGRVG VCIAT SGPGA TNLVS ALADA LLDSV PMVAI TGQVP RRMIG TDAFQ ETPIV
```

FIG.8A

```
                190        200        210        220        230        240
XI12/8A   EVTRS ITKHN YLVLD VDDIP RVVQE AFFLA SSGRP GPVLV DIPKD IQQQM AVPVW DKPMS

W22/1A    EVTRS ITKHN YLVLD VDDIP RVVQE AFFLA SSGRP GPVLV DIPKD IQQQM AVPVW DKPMS
          11111 11111 11111 11111 11111 11111 11111 11111 11111 11111 11111 11111
B73/7-4   EVTRS ITKHN YLVLD VDDIP RVVQE AFFLA SSGRP GPVLV DIPKD IQQQM AVPVW DKPMS
          11111 11111 11111 11111 11111 11111 11111 11111 11111 11111 11111 11111
XI12/8A   EVTRS ITKHN YLVLD VDDIP RVVQE AFFLA SSGRP GPVLV DIPKD IQQQM AVPVW DKPMS

                250        260        270        280        290        300
XI12/8A   LPGYI ARLPK PPATE LLEQV LRLVG ESRRP VLYVG GGCAA SGEEL RRFVE LTGIP VTTTL

W22/1A    LPGYI ARLPK PPATE LLEQV LRLVG ESRRP VLYVG GGCAA SGEEL RRFVE LTGIP VTTTL
          11111 11111 11111 11111 11111 11111 11111 11111 11111 11111 11111 11111
B73/7-4   LPGYI ARLPK PPATE LLEQV LRLVG ESRRP VLYVG GGCAA SGEEL RRFVE LTGIP VTTTL
          11111 11111 11111 11111 11111 11111 11111 11111 11111 11111 11111 11111
XI12/8A   LPGYI ARLPK PPATE LLEQV LRLVG ESRRP VLYVG GGCAA SGEEL RRFVE LTGIP VTTTL

                310        320        330        340        350        360
XI12/8A   MGLGN FPSDD PLSLR MLGMH GTVYA NYAVD KADLL LALGV RFDDR VTGKI EAFAS RAKIV

W22/1A    MGLGN FPSDD PLSLR MLGMH GTVYA NYAVD KADLL LALGV RFDDR VTGKI EAFAS RAKIV
          11111 11111 11111 11111 11111 11111 11111 11111 11111 11111 11111 11111
B73/7-4   MGLGN FPSDD PLSLR MLGMH GTVYA NYAVD KADLL LALGV RFDDR VTGKI EAFAS RAKIV
          11111 11111 11111 11111 11111 11111 11111 11111 11111 11111 11111 11111
XI12/8A   MGLGN FPSDD PLSLR MLGMH GTVYA NYAVD KADLL LALGV RFDDR VTGKI EAFAS RAKIV
```

FIG.8B

```
                     370        380        390        400        410        420
XI12/8A   HVDID PAEIG KNKQP HVSIC ADVKL ALQGM NALLE GSTSK KSFDF GSWND ELDQQ KREFP

W22/1A    HVDID PAEIG KNKQP HVSIC ADVKL ALQGM NALLE GSTSK KSFDF GSWND ELDQQ KREFP
          11111 11111 11111 11111 11111 11111 11111 11111 11111 11111 11111 11111
B73/7-4   HVDID PAEIG KNKQP HVSIC ADVKL ALQGM NALLE GSTSK KSFDF GSWND ELDQQ KREFP
          11111 11111 11111 11111 11111 11111 11111 11111 11111 11111 11111 11111
XI12/8A   HVDID PAEIG KNKQP HVSIC ADVKL ALQGM NALLE GSTSK KSFDF GSWND ELDQQ KREFP

                     430        440        450        460        470        480
XI12/8A   LGYKT SNEEI QPQYA IQVLD ELTKG EAIIG TGVGQ HQMWA AQYYT YKRPR QWLSS AGLGA

W22/1A    LGYKT SNEEI QPQYA IQVLD ELTKG EAIIG TGVGQ HQMWA AQYYT YKRPR QWLSS AGLGA
          11111 11111 11111 11111 11111 11111 11111 11111 11111 11111 11111 11111
B73/7-4   LGYKT SNEEI QPQYA IQVLD ELTKG EAIIG TGVGQ HQMWA AQYYT YKRPR QWLSS AGLGA
          11111 11111 11111 11111 11111 11111 11111 11111 11111 11111 11111 11111
XI12/8A   LGYKT SNEEI QPQYA IQVLD ELTKG EAIIG TGVGQ HQMWA AQYYT YKRPR QWLSS AGLGA

                     490        500        510        520        530        540
XI12/8A   MGFGL PAAAG ASVAN PGVTV VDIDG DGSFL MNVQE LAMIR IENLP VKVFV LNNQH LGNVV

W22/1A    MGFGL PAAAG ASVAN PGVTV VDIDG DGSFL MNVQE LAMIR IENLP VKVFV LNNQH LGNVV
          11111 11111 11111 11111 11111 11111 11111 11111 11111 11111 11111 11111
B73/7-4   MGFGL PAAAG ASVAN PGVTV VDIDG DGSFL MNVQE LAMIR IENLP VKVFV LNNQH LGNVV
          11111 11111 11111 11111 11111 11111 11111 11111 11111 11111 11111 11111
XI12/8A   MGFGL PAAAG ASVAN PGVTV VDIDG DGSFL MNVQE LAMIR IENLP VKVFV LNNQH LGNVV
```

FIG.8C

```
                   550         560         570         580         590         600
XI12/8A  QWEDR FYKAN RAHTY LGNPE NESEI YPDFV TIAKG FNIPA VRVTK KNEVR AAIKK MLETP
          #
W22/1A   QWEDR FYKAN RAHTY LGNPE NESEI YPDFV TIAKG FNIPA VRVTK KNEVR AAIKK MLETP
         1 111 11111 11111 11111 11111 11111 11111 11111 11111 11111 11111 11111
B73/7-4  QIEDR FYKAN RAHTY LGNPE NESEI YPDFV TIAKG FNIPA VRVTK KNEVR AAIKK MLETP
         1 111 11111 11111 11111 11111 11111 11111 11111 11111 11111 11111 11111
XI12/8A  QWEDR FYKAN RAHTY LGNPE NESEI YPDFV TIAKG FNIPA VRVTK KNEVR AAIKK MLETP

                   610         620         630
XI12/8A  GPYLL DIIVP HQEHV LPMIP NGGAF KDMIL DGDGR TVY*
                                *
W22/1A   GPYLL DIIVP HQEHV LPMIP sGGAF KDMIL DGDGR TVY>
         11111 11111 11111 11111 11111 11111 11111 111
B73/7-4  GPYLL DIIVP HQEHV LPMIP sGGAF KDMIL DGDGR TVY>
         11111 11111 11111 11111  1111 11111 11111 111
XI12/8A  GPYLL DIIVP HQEHV LPMIP NGGAF KDMIL DGDGR TVY
```

FIG.8D

SEQUENCE LISTING

```
(1) GENERAL INFORMATION:

   (iii) NUMBER OF SEQUENCES: 3


(2) INFORMATION FOR SEQ ID NO: 1:

     (i) SEQUENCE CHARACTERISTICS:
          (A) LENGTH: 1969 BP's and 638 Amino Acids
          (B) TYPE: Nucleotide and Amino Acid
```

-continued

```
        (C) STRANDEDNESS: Single
        (D) TOPOLOGY: Linear

    (ii) MOLECULE TYPE: DNA and Protein

    (xi) SEQUENCE DESCRIPTION: SEQ ID NO: 1:

AACCCTCGCG CCGCCTCCGA GACAGCCGCC GCAACC                            36

ATG GCC ACC GCC GCC GCC GCG TCT ACC GCG CTC ACT                    72
Met Ala Thr Ala Ala Ala Ala Ser Thr Ala Leu Thr
  1               5                  10

GGC GCC ACT ACC GCT GCG CCC AAG GCG AGG CGC CGG                   108
Gly Ala Thr Thr Ala Ala Pro Lys Ala Arg Arg Arg
        15                  20

GCG CAC CTC CTG GCC ACC CGC CGC GCC CTC GCC GCG                   144
Ala His Leu Leu Ala Thr Arg Arg Ala Leu Ala Ala
 25                  30                  35

CCC ATC AGG TGC TCA GCG GCG TCA CCC GCC ATG CCG                   180
Pro Ile Arg Cys Ser Ala Ala Ser Pro Ala Met Pro
            40                  45

ATG GCT CCC CCG GCC ACC CCG CTC CGG CCG TGG GGC                   216
Met Ala Pro Pro Ala Thr Pro Leu Arg Pro Trp Gly
     50                  55                  60

CCC ACC GAT CCC CGC AAG GGC GCC GAC ATC CTC GTC                   252
Pro Thr Asp Pro Arg Lys Gly Ala Asp Ile Leu Val
                65                  70

GAG TCC CTC GAG CGC TGC GGC GTC CGC GAC GTC TTC                   288
Glu Ser Leu Glu Arg Cys Gly Val Arg Asp Val Phe
        75                  80

GCC TAC CCC GGC GGC GCG TCC ATG GAG ATC CAC CAG                   324
Ala Tyr Pro Gly Gly Ala Ser Met Glu Ile His Gln
 85                  90                  95

GCA CTC ACC CGC TCC CCC GTC ATC GCC AAC CAC CTC                   360
Ala Leu Thr Arg Ser Pro Val Ile Ala Asn His Leu
            100                 105

TTC CGC CAC GAG CAA GGG GAG GCC TTT GCG GCC TCC                   396
Phe Arg His Glu Gln Gly Glu Ala Phe Ala Ala Ser
    110                 115                 120

GGC TAC GCG CGC TCC TCG GGC CGC GTC GGC GTC TGC                   432
Gly Tyr Ala Arg Ser Ser Gly Arg Val Gly Val Cys
                125                 130

ATC GCC ACC TCC GGC CCC GGC GCC ACC AAC CTT GTC                   468
Ile Ala Thr Ser Gly Pro Gly Ala Thr Asn Leu Val
        135                 140

TCC GCG CTC GCC GAC GCG CTG CTC GAT TCC GTC CCC                   504
Ser Ala Leu Ala Asp Ala Leu Leu Asp Ser Val Pro
145                 150                 155

ATG GTC GCC ATC ACG GGA CAG GTG CCG CGA CGC ATG                   540
Met Val Ala Ile Thr Gly Gln Val Pro Arg Arg Met
            160                 165

ATT GGC ACC GAC GCC TTC CAG GAG ACG CCC ATC GTC                   576
Ile Gly Thr Asp Ala Phe Gln Glu Thr Pro Ile Val
    170                 175                 180

GAG GTC ACC CGC TCC ATC ACC AAG CAC AAC TAC CTG                   612
Glu Val Thr Arg Ser Ile Thr Lys His Asn Tyr Leu
                185                 190

GTC CTC GAC GTC GAC GAC ATC CCC CGC GTC GTG CAG                   648
Val Leu Asp Val Asp Asp Ile Pro Arg Val Val Gln
        195                 200

GAG GCT TTC TTC CTC GCC TCC TCT GGT CGA CCG GGG                   684
Glu Ala Phe Phe Leu Ala Ser Ser Gly Arg Pro Gly
```

-continued

```
205                 210                 215

CCG GTG CTT GTC GAC ATC CCC AAG GAC ATC CAG CAG                          720
Pro Val Leu Val Asp Ile Pro Lys Asp Ile Gln Gln
            220                 225

CAG ATG GCG GTG CCT GTC TGG GAC AAG CCC ATG AGT                          756
Gln Met Ala Val Pro Val Trp Asp Lys Pro Met Ser
    230                 235                 240

CTG CCT GGG TAC ATT GCG CGC CTT CCC AAG CCC CCT                          792
Leu Pro Gly Tyr Ile Ala Arg Leu Pro Lys Pro Pro
                245                 250

GCG ACT GAG TTG CTT GAG CAG GTG CTG CGT CTT GTT                          828
Ala Thr Glu Leu Leu Glu Gln Val Leu Arg Leu Val
        255                 260

GGT GAA TCC CGG CGC CCT GTT CTT TAT GTT GGC GGT                          864
Gly Glu Ser Arg Arg Pro Val Leu Tyr Val Gly Gly
265                 270                 275

GCG TGC GCA GCA TCT GGT GAG GAG TTG CGA CGC TTT                          900
Ala Cys Ala Ala Ser Gly Glu Glu Leu Arg Arg Phe
            280                 285

GTG GAG CTG ACT GGA ATC CCG GTC ACA ACT ACT CTT                          936
Val Glu Leu Thr Gly Ile Pro Val Thr Thr Thr Leu
    290                 295                 300

ATG GGC CTC GGC AAC TTC CCC AGC GAC GAC CCA CTG                          972
Met Gly Leu Gly Asn Phe Pro Ser Asp Asp Pro Leu
                305                 310

TCT CTG CGC ATG CTA GGT ATG CAT GGC ACG GTG TAT                         1008
Ser Leu Arg Met Leu Gly Met His Gly Thr Val Tyr
        315                 320

GCA AAT TAT GCA GTG GAT AAG GCC GAT CTG TTG CTT                         1044
Ala Asn Tyr Ala Val Asp Lys Ala Asp Leu Leu Leu
325                 330                 335

GCA CTT GGT GTG CGG TTT GAT GAT CGT GTG ACA GGG                         1080
Ala Leu Gly Val Arg Phe Asp Asp Arg Val Thr Gly
            340                 345

AAG ATT GAG GCT TTT GCA AGC AGG GCT AAG ATT GTG                         1116
Lys Ile Glu Ala Phe Ala Ser Arg Ala Lys Ile Val
    350                 355                 360

CAC GTT GAT ATT GAT CCG GCT GAG ATT GGC AAG AAC                         1152
His Val Asp Ile Asp Pro Ala Glu Ile Gly Lys Asn
                365                 370

AAG CAG CCA CAT GTG TCC ATC TGT GCA GAT GTT AAG                         1188
Lys Gln Pro His Val Ser Ile Cys Ala Asp Val Lys
        375                 380

CTT GCT TTG CAG GGC ATG AAT GCT CTT CTT GAA GGA                         1224
Leu Ala Leu Gln Gly Met Asn Ala Leu Leu Glu Gly
385                 390                 395

AGC ACA TCA AAG AAG AGC TTT GAC TTT GGC TCA TGG                         1260
Ser Thr Ser Lys Lys Ser Phe Asp Phe Gly Ser Trp
            400                 405

AAC GAT GAG TTG GAT CAG CAG AAG AGG GAA TTC CCC                         1296
Asn Asp Glu Leu Asp Gln Gln Lys Arg Glu Phe Pro
    410                 415                 420

CTT GGG TAT AAA ACA TCT AAT GAG GAG ATC CAG CCA                         1332
Leu Gly Tyr Lys Thr Ser Asn Glu Glu Ile Gln Pro
                425                 430

CAA TAT GCT ATT CAG GTT CTT GAT GAG CTG ACG AAA                         1368
Gln Tyr Ala Ile Gln Val Leu Asp Glu Leu Thr Lys
        435                 440

GGC GAG GCC ATC ATC GGC ACA GGT GTT GGG CAG CAC                         1404
```

-continued

```
Gly Glu Ala Ile Ile Gly Thr Gly Val Gly Gln His
445                 450                 455

CAT ATG TGG GCG GCA CAG TAC TAC ACT TAC AAG CGG                    1440
Gln Met Trp Ala Ala Gln Tyr Tyr Thr Tyr Lys Arg
            460                 465

CCA AGG CAG TGG TTG TCT TCA GCT GGT CTT GGG GCT                    1476
Pro Arg Gln Trp Leu Ser Ser Ala Gly Leu Gly Ala
    470                 475                 480

ATG GGA TTT GGT TTG CCG GCT GCT GCT GGT GCT TCT                    1512
Met Gly Phe Gly Leu Pro Ala Ala Ala Gly Ala Ser
                485                 490

GTG GCC AAC CCA GGT GTT ACT GTT GTT GAC ATC GAT                    1548
Val Ala Asn Pro Gly Val Thr Val Val Asp Ile Asp
        495                 500

GGA GAT GGT AGC TTT CTC ATG AAC GTT CAG GAG CTA                    1584
Gly Asp Gly Ser Phe Leu Met Asn Val Gln Glu Leu
505                 510                 515

GCT ATG ATC CGA ATT GAG AAC CTC CCG GTG AAG GTC                    1620
Ala Met Ile Arg Ile Glu Asn Leu Pro Val Lys Val
            520                 525

TTT GTG CTA AAC AAC CAG CAC CTG GGG ATG GTG GTG                    1656
Phe Val Leu Asn Asn Gln His Leu Gly Met Val Val
    530                 535                 540

CAG TGG GAG GAC AGG TTC TAT AAG GCC AAC AGA GCG                    1692
Gln Trp Glu Asp Arg Phe Tyr Lys Ala Asn Arg Ala
                545                 550

CAC ACA TAC TTG GGA AAC CCA GAG AAT GAA AGT GAG                    1728
His Thr Tyr Leu Gly Asn Pro Glu Asn Glu Ser Glu
        555                 560

ATA TAT CCA GAT TTC GTG ACG ATC GCC AAA GGG TTC                    1764
Ile Tyr Pro Asp Phe Val Thr Ile Ala Lys Gly Phe
565                 570                 575

AAC ATT CCA GCG GTC CGT GTG ACA AAG AAG AAC GAA                    1800
Asn Ile Pro Ala Val Arg Val Thr Lys Lys Asn Glu
            580                 585

GTC CGC GCA GCG ATA AAG AAG ATG CTC GAG ACT CCA                    1836
Val Arg Ala Ala Ile Lys Lys Met Leu Glu Thr Pro
    590                 595                 600

GGG CCG TAC CTC TTG GAT ATA ATC GTC CCA CAC CAG                    1872
Gly Pro Tyr Leu Leu Asp Ile Ile Val Pro His Gln
                605                 610

GAG CAT GTG TTG CCT ATG ATC CCT AAT GGT GGG GCT                    1908
Glu His Val Leu Pro Met Ile Pro Asn Gly Gly Ala
        615                 620

TTC AAG GAT ATG ATC CTG GAT GGT GAT GGC AGG ACT                    1944
Phe Lys Asp Met Ile Leu Asp Gly Asp Gly Arg Thr
625                 630                 635

GTG TAC                                                            1950
Val Tyr
    638

TGATCTAAAA TCCAGCAAG                                               1969
```

(2) INFORMATION FOR SEQ ID NO: 2:

(i) SEQUENCE CHARACTERISTICS:
(A) LENGTH: 1969 BP's and 638 Amino Acids
(B) TYPE: Nucleotide and Amino Acid
(C) STRANDEDNESS: Single
(D) TOPOLOGY: Linear (ii) MOLECULE TYPE: DNA and Protein -continued

```
    (xi) SEQUENCE DESCRIPTION: SEQ ID NO: 2:

AACCCTCGCG CCGCCTCCGA GACAGCCGCC GCAACC                            36

ATG GCC ACC GCC GCC GCC GCG TCT ACC GCG CTC ACT                    72
Met Ala Thr Ala Ala Ala Ala Ser Thr Ala Leu Thr
  1               5                  10

GGC GCC ACT ACC GCT GCG CCC AAG GCG AGG CGC CGG                   108
Gly Ala Thr Thr Ala Ala Pro Lys Ala Arg Arg Arg
         15                  20

GCG CAC CTC CTG GCC ACC CGC CGC GCC CTC GCC GCG                   144
Ala His Leu Leu Ala Thr Arg Arg Ala Leu Ala Ala
 25                  30                  35

CCC ATC AGG TGC TCA GCG GCG TCA CCC GCC ATG CCG                   180
Pro Ile Arg Cys Ser Ala Ala Ser Pro Ala Met Pro
             40                  45

ATG GCT CCC CCG GCC ACC CCG CTC CGG CCG TGG GGC                   216
Met Ala Pro Pro Ala Thr Pro Leu Arg Pro Trp Gly
     50                  55                  60

CCC ACC GAT CCC CGC AAG GGC GCC GAC ATC CTC GTC                   252
Pro Thr Asp Pro Arg Lys Gly Ala Asp Ile Leu Val
                 65                  70

GAG TCC CTC GAG CGC TGC GGC GTC CGC GAC GTC TTC                   288
Glu Ser Leu Glu Arg Cys Gly Val Arg Asp Val Phe
         75                  80

GCC TAC CCC GGC GGC GCG TCC ATG GAG ATC CAC CAG                   324
Ala Tyr Pro Gly Gly Ala Ser Met Glu Ile His Gln
 85                  90                  95

GCA CTC ACC CGC TCC CCC GTC ATC GCC AAC CAC CTC                   360
Ala Leu Thr Arg Ser Pro Val Ile Ala Asn His Leu
            100                 105

TTC CGC CAC GAG CAA GGG GAG GCC TTT GCG GCC TCC                   396
Phe Arg His Glu Gln Gly Glu Ala Phe Ala Ala Ser
    110                 115                 120

GGC TAC GCG CGC TCC TCG GGC CGC GTC GGC GTC TGC                   432
Gly Tyr Ala Arg Ser Ser Gly Arg Val Gly Val Cys
                125                 130

ATC GCC ACC TCC GGC CCC GGC GCC ACC AAC CTT GTC                   468
Ile Ala Thr Ser Gly Pro Gly Ala Thr Asn Leu Val
        135                 140

TCC GCG CTC GCC GAC GCG CTG CTC GAT TCC GTC CCC                   504
Ser Ala Leu Ala Asp Ala Leu Leu Asp Ser Val Pro
145                 150                 155

ATG GTC GCC ATC ACG GGA CAG GTG CCG CGA CGC ATG                   540
Met Val Ala Ile Thr Gly Gln Val Pro Arg Arg Met
            160                 165

ATT GGC ACC GAC GCC TTC CAG GAG ACG CCC ATC GTC                   576
Ile Gly Thr Asp Ala Phe Gln Glu Thr Pro Ile Val
    170                 175                 180

GAG GTC ACC CGC TCC ATC ACC AAG CAC AAC TAC CTG                   612
Glu Val Thr Arg Ser Ile Thr Lys His Asn Tyr Leu
                185                 190

GTC CTC GAC GTC GAC GAC ATC CCC CGC GTC GTG CAG                   648
Val Leu Asp Val Asp Asp Ile Pro Arg Val Val Gln
        195                 200

GAG GCT TTC TTC CTC GCC TCC TCT GGT CGA CCG GGG                   684
Glu Ala Phe Phe Leu Ala Ser Ser Gly Arg Pro Gly
205                 210                 215

CCG GTG CTT GTC GAC ATC CCC AAG GAC ATC CAG CAG                   720
Pro Val Leu Val Asp Ile Pro Lys Asp Ile Gln Gln
```

-continued

```
            220                 225

CAG ATG GCG GTG CCT GTC TGG GAC AAG CCC ATG AGT                756
Gln Met Ala Val Pro Val Trp Asp Lys Pro Met Ser
    230                 235                 240

CTG CCT GGG TAC ATT GCG CGC CTT CCC AAG CCC CCT                792
Leu Pro Gly Tyr Ile Ala Arg Leu Pro Lys Pro Pro
                245                 250

GCG ACT GAG TTG CTT GAG CAG GTG CTG CGT CTT GTT                828
Ala Thr Glu Leu Leu Glu Gln Val Leu Arg Leu Val
        255                 260

GGT GAA TCC CGG CGC CCT GTT CTT TAT GTT GGC GGT                864
Gly Glu Ser Arg Arg Pro Val Leu Tyr Val Gly Gly
265                 270                 275

GCG TGC GCA GCA TCT GGT GAG GAG TTG CGA CGC TTT                900
Ala Cys Ala Ala Ser Gly Glu Glu Leu Arg Arg Phe
            280                 285

GTG GAG CTG ACT GGA ATC CCG GTC ACA ACT ACT CTT                936
Val Glu Leu Thr Gly Ile Pro Val Thr Thr Thr Leu
    290                 295                 300

ATG GGC CTC GGC AAC TTC CCC AGC GAC GAC CCA CTG                972
Met Gly Leu Gly Asn Phe Pro Ser Asp Asp Pro Leu
                305                 310

TCT CTG CGC ATG CTA GGT ATG CAT GGC ACG GTG TAT               1008
Ser Leu Arg Met Leu Gly Met His Gly Thr Val Tyr
        315                 320

GCA AAT TAT GCA GTG GAT AAG GCC GAT CTG TTG CTT               1044
Ala Asn Tyr Ala Val Asp Lys Ala Asp Leu Leu Leu
325                 330                 335

GCA CTT GGT GTG CGG TTT GAT GAT CGT GTG ACA GGG               1080
Ala Leu Gly Val Arg Phe Asp Asp Arg Val Thr Gly
            340                 345

AAG ATT GAG GCT TTT GCA AGC AGG GCT AAG ATT GTG               1116
Lys Ile Glu Ala Phe Ala Ser Arg Ala Lys Ile Val
    350                 355                 360

CAC GTT GAT ATT GAT CCG GCT GAG ATT GGC AAG AAC               1152
His Val Asp Ile Asp Pro Ala Glu Ile Gly Lys Asn
                365                 370

AAG CAG CCA CAT GTG TCC ATC TGT GCA GAT GTT AAG               1188
Lys Gln Pro His Val Ser Ile Cys Ala Asp Val Lys
        375                 380

CTT GCT TTG CAG GGC ATG AAT GCT CTT CTT GAA GGA               1224
Leu Ala Leu Gln Gly Met Asn Ala Leu Leu Glu Gly
385                 390                 395

AGC ACA TCA AAG AAG AGC TTT GAC TTT GGC TCA TGG               1260
Ser Thr Ser Lys Lys Ser Phe Asp Phe Gly Ser Trp
            400                 405

AAC GAT GAG TTG GAT CAG CAG AAG AGG GAA TTC CCC               1296
Asn Asp Glu Leu Asp Gln Gln Lys Arg Glu Phe Pro
    410                 415                 420

CTT GGG TAT AAA ACA TCT AAT GAG GAG ATC CAG CCA               1332
Leu Gly Tyr Lys Thr Ser Asn Glu Glu Ile Gln Pro
                425                 430

CAA TAT GCT ATT CAG GTT CTT GAT GAG CTG ACG AAA               1368
Gln Tyr Ala Ile Gln Val Leu Asp Glu Leu Thr Lys
        435                 440

GGC GAG GCC ATC ATC GGC ACA GGT GTT GGG CAG CAC               1404
Gly Glu Ala Ile Ile Gly Thr Gly Val Gly Gln His
445                 450                 455

CAT ATG TGG GCG GCA CAG TAC TAC ACT TAC AAG CGG               1440
```

-continued

```
Gln Met Trp Ala Ala Gln Tyr Tyr Thr Tyr Lys Arg
            460                 465

CCA AGG CAG TGG TTG TCT TCA GCT GGT CTT GGG GCT                   1476
Pro Arg Gln Trp Leu Ser Ser Ala Gly Leu Gly Ala
    470                 475                 480

ATG GGA TTT GGT TTG CCG GCT GCT GCT GGT GCT TCT                   1512
Met Gly Phe Gly Leu Pro Ala Ala Ala Gly Ala Ser
                485                 490

GTG GCC AAC CCA GGT GTT ACT GTT GTT GAC ATC GAT                   1548
Val Ala Asn Pro Gly Val Thr Val Val Asp Ile Asp
        495                 500

GGA GAT GGT AGC TTT CTC ATG AAC GTT CAG GAG CTA                   1584
Gly Asp Gly Ser Phe Leu Met Asn Val Gln Glu Leu
505                 510                 515

GCT ATG ATC CGA ATT GAG AAC CTC CCG GTG AAG GTC                   1620
Ala Met Ile Arg Ile Glu Asn Leu Pro Val Lys Val
            520                 525

TTT GTG CTA AAC AAC CAG CAC CTG GGG ATG GTG GTG                   1656
Phe Val Leu Asn Asn Gln His Leu Gly Met Val Val
    530                 535                 540

CAG TGG GAG GAC AGG TTC TAT AAG GCC AAC AGA GCG                   1692
Gln Trp Glu Asp Arg Phe Tyr Lys Ala Asn Arg Ala
                545                 550

CAC ACA TAC TTG GGA AAC CCA GAG AAT GAA AGT GAG                   1728
His Thr Tyr Leu Gly Asn Pro Glu Asn Glu Ser Glu
        555                 560

ATA TAT CCA GAT TTC GTG ACG ATC GCC AAA GGG TTC                   1764
Ile Tyr Pro Asp Phe Val Thr Ile Ala Lys Gly Phe
565                 570                 575

AAC ATT CCA GCG GTC CGT GTG ACA AAG AAG AAC GAA                   1800
Asn Ile Pro Ala Val Arg Val Thr Lys Lys Asn Glu
            580                 585

GTC CGC GCA GCG ATA AAG AAG ATG CTC GAG ACT CCA                   1836
Val Arg Ala Ala Ile Lys Lys Met Leu Glu Thr Pro
    590                 595                 600

GGG CCG TAC CTC TTG GAT ATA ATC GTC CCA CAC CAG                   1872
Gly Pro Tyr Leu Leu Asp Ile Ile Val Pro His Gln
                605                 610

GAG CAT GTG TTG CCT ATG ATC CCT AGT GGT GGG GCT                   1908
Glu His Val Leu Pro Met Ile Pro Ser Gly Gly Ala
        615                 620

TTC AAG GAT ATG ATC CTG GAT GGT GAT GGC AGG ACT                   1944
Phe Lys Asp Met Ile Leu Asp Gly Asp Gly Arg Thr
625                 630                 635

GTG TAC                                                           1950
Val Tyr
    638

TGATCTAAAA TCCAGCAAG                                              1969
```

(2) INFORMATION FOR SEQ ID NO: 3:

(i) SEQUENCE CHARACTERISTICS:
- (A) LENGTH: 1969 BP's and 638 Amino Acids
- (B) TYPE: Nucleotide and Amino Acid
- (C) STRANDEDNESS: Single
- (D) TOPOLOGY: Linear (ii) MOLECULE TYPE: DNA and Protein (xi) SEQUENCE DESCRIPTION: SEQ ID NO: 3:

```
AACCCTCGCG CCGCCTCCGA GACAGCCGCC GCAACC                              36
```

-continued

```
ATG GCC ACC GCC GCC GCC GCG TCT ACC GCG CTC ACT                        72
Met Ala Thr Ala Ala Ala Ala Ser Thr Ala Leu Thr
  1               5                  10

GGC GCC ACT ACC GCT GCG CCC AAG GCG AGG CGC CGG                       108
Gly Ala Thr Thr Ala Ala Pro Lys Ala Arg Arg Arg
         15                  20

GCG CAC CTC CTG GCC ACC CGC CGC GCC CTC GCC GCG                       144
Ala His Leu Leu Ala Thr Arg Arg Ala Leu Ala Ala
 25                  30                  35

CCC ATC AGG TGC TCA GCG GCG TCA CCC GCC ATG CCG                       180
Pro Ile Arg Cys Ser Ala Ala Ser Pro Ala Met Pro
             40                  45

ATG GCT CCC CCG GCC ACC CCG CTC CGG CCG TGG GGC                       216
Met Ala Pro Pro Ala Thr Pro Leu Arg Pro Trp Gly
     50                  55                  60

CCC ACC GAG CCC CGC AAG GGT GCT GAC ATC CTC GTC                       252
Pro Thr Glu Pro Arg Lys Gly Ala Asp Ile Leu Val
                 65                  70

GAG TCC CTC GAG CGC TGC GGC GTC CGC GAC GTC TTC                       288
Glu Ser Leu Glu Arg Cys Gly Val Arg Asp Val Phe
         75                  80

GCC TAC CCC GGC GGC GCG TCC ATG GAG ATC CAC CAG                       324
Ala Tyr Pro Gly Gly Ala Ser Met Glu Ile His Gln
 85                  90                  95

GCA CTC ACC CGC TCC CCC GTC ATC GCC AAC CAC CTC                       360
Ala Leu Thr Arg Ser Pro Val Ile Ala Asn His Leu
            100                 105

TTC CGC CAC GAG CAA GGG GAG GCC TTT GCC GCC TCC                       396
Phe Arg His Glu Gln Gly Glu Ala Phe Ala Ala Ser
    110                 115                 120

GGC TAC GCG CGC TCC TCG GGC CGC GTC GGC GTC TGC                       432
Gly Tyr Ala Arg Ser Ser Gly Arg Val Gly Val Cys
                125                 130

ATC GCC ACC TCC GGC CCC GGC GCC ACC AAC CTA GTC                       468
Ile Ala Thr Ser Gly Pro Gly Ala Thr Asn Leu Val
        135                 140

TCC GCG CTC GCC GAC GCG CTG CTC GAT TCC GTC CCC                       504
Ser Ala Leu Ala Asp Ala Leu Leu Asp Ser Val Pro
145                 150                 155

ATG GTC GCC ATC ACG GGA CAG GTG CCG CGA CGC ATG                       540
Met Val Ala Ile Thr Gly Gln Val Pro Arg Arg Met
            160                 165

ATT GGC ACC GAC GCC TTC CAG GAG ACG CCC ATC GTC                       576
Trp Gly Thr Asp Ala Phe Gln Glu Thr Pro Ile Val
    170                 175                 180

GAG GTC ACC CGC TCC ATC ACC AAG CAC AAC TAC CTG                       612
Glu Val Thr Arg Ser Ile Thr Lys His Asn Tyr Leu
                185                 190

GTC CTC GAC GTC GAC GAC ATC CCC CGC GTC GTG CAG                       648
Val Leu Asp Val Asp Asp Ile Pro Arg Val Val Gln
        195                 200

GAG GCT TTC TTC CTC GCC TCC TCT GGT CGA CCA GGG                       684
Glu Ala Phe Phe Leu Ala Ser Ser Gly Arg Pro Gly
205                 210                 215

CCG GTG CTT GTC GAC ATC CCC AAG GAC ATC CAG CAG                       720
Pro Val Leu Val Asp Ile Pro Lys Asp Ile Gln Gln
            220                 225

CAG ATG GCG GTG CCT GTC TGG GAC AAG CCC ATG AGT                       756
Gln Met Ala Val Pro Val Trp Asp Lys Pro Met Ser
```

-continued

```
    230                 235                 240

CTG CCT GGG TAC ATT GCG CGC CTT CCC AAG CCC CCT                   792
Leu Pro Gly Tyr Ile Ala Arg Leu Pro Lys Pro Pro
                245                 250

GCG ACT GAG TTG CTT GAG CAG GTG CTG CGT CTT GTT                   828
Ala Thr Glu Leu Leu Glu Gln Val Leu Arg Leu Val
        255                 260

GGT GAA TCG CGG CGC CCT GTT CTT TAT GTG GGC GGT                   864
Gly Glu Ser Arg Arg Pro Val Leu Tyr Val Gly Gly
265                 270                 275

GCG TGC GCA GCA TCT GGT GAG GAG TTG CGA CGC TTT                   900
Ala Cys Ala Ala Ser Gly Glu Glu Leu Arg Arg Phe
            280                 285

GTG GAG CTG ACT GGA ATC CCG GTC ACA ACT ACT CTT                   936
Val Glu Leu Thr Gly Ile Pro Val Thr Thr Thr Leu
    290                 295                 300

ATG GGC CTC GGC AAC TTC CCC AGC GAC GAC CCA CTG                   972
Met Gly Leu Gly Asn Phe Pro Ser Asp Asp Pro Leu
                305                 310

TCT CTG CGC ATG CTA GGT ATG CAT GGG ACG GTG TAT                  1008
Ser Leu Arg Met Leu Gly Met His Gly Thr Val Tyr
        315                 320

GCA AAT TAT GCA GTG GAT AAG GCC GAT CTG TTG CTT                  1044
Ala Asn Tyr Ala Val Asp Lys Ala Asp Leu Leu Leu
325                 330                 335

GCA CTT GGT GTG CGG TTT GAT GAT CGT GTG ACA GGG                  1080
Ala Leu Gly Val Arg Phe Asp Asp Arg Val Thr Gly
            340                 345

AAG ATT GAG GCT TTT GCA AGC AGG GCT AAG ATT GTG                  1116
Lys Ile Glu Ala Phe Ala Ser Arg Ala Lys Ile Val
    350                 355                 360

CAC GTT GAT ATT GAT CCG GCT GAG ATT GGC AAG AAC                  1152
His Val Asp Ile Asp Pro Ala Glu Ile Gly Lys Asn
                365                 370

AAG CAG CCA CAT GTG TCC ATC TGT GCA GAT GTT AAG                  1188
Lys Gln Pro His Val Ser Ile Cys Ala Asp Val Lys
        375                 380

CTT GCT TTG CAG GGC ATG AAT GCT CTT CTT GAA GGA                  1224
Leu Ala Leu Gln Gly Met Asn Ala Leu Leu Glu Gly
385                 390                 395

AGC ACA TCA AAG AAG AGC TTT GAC TTT GGC TCA TGG                  1260
Ser Thr Ser Lys Lys Ser Phe Asp Phe Gly Ser Trp
            400                 405

AAC GAT GAG TTG GAT CAG CAG AAG AGG GAA TTC CCC                  1296
Asn Asp Glu Leu Asp Gln Gln Lys Arg Glu Phe Pro
    410                 415                 420

CTT GGG TAT AAA ACA TCT AAT GAG GAG ATC CAG CCA                  1332
Leu Gly Tyr Lys Thr Ser Asn Glu Glu Ile Gln Pro
                425                 430

CAA TAT GCT ATT CAG GTT CTT GAT GAG CTG ACG AAA                  1368
Gln Tyr Ala Ile Gln Val Leu Asp Glu Leu Thr Lys
        435                 440

GGC GAG GCC ATC ATC GGC ACA GGT GTT GGG CAG CAC                  1404
Gly Glu Ala Ile Ile Gly Thr Gly Val Gly Gln His
445                 450                 455

CAT ATG TGG GCG GCA CAG TAC TAC ACT TAC AAG CGG                  1440
Gln Met Trp Ala Ala Gln Tyr Tyr Thr Tyr Lys Arg
            460                 465

CCA AGG CAG TGG TTG TCT TCA GCT GGT CTT GGG GCT                  1476
```

-continued

```
Pro Arg Gln Trp Leu Ser Ser Ala Gly Leu Gly Ala
    470                 475                 480

ATG GGA TTT GGT TTG CCG GCT GCT GCT GGT GCT TCT                1512
Met Gly Phe Gly Leu Pro Ala Ala Ala Gly Ala Ser
                485                 490

GTG GCC AAC CCA GGT GTC ACT GTT GTT GAC ATC GAT                1548
Val Ala Asn Pro Gly Val Thr Val Val Asp Ile Asp
        495                 500

GGA GAT GGT AGC TTT CTC ATG AAC GTT CAG GAG CTA                1584
Gly Asp Gly Ser Phe Leu Met Asn Val Gln Glu Leu
505                 510                 515

GCT ATG ATC CGA ATT GAG AAC CTC CCA GTG AAG GTC                1620
Ala Met Ile Arg Ile Glu Asn Leu Pro Val Lys Val
            520                 525

TTT GTG CTA AAC AAC CAG CAC CTG GGG ATG GTG GTG                1656
Phe Val Leu Asn Asn Gln His Leu Gly Met Val Val
    530                 535                 540

CAG TGG GAG GAC AGG TTC TAT AAG GCC AAC AGA GCG                1692
Gln Trp Glu Asp Arg Phe Tyr Lys Ala Asn Arg Ala
                545                 550

CAC ACA TAC TTG GGA AAC CCA GAG AAT GAA AGT GAG                1728
His Thr Tyr Leu Gly Asn Pro Glu Asn Glu Ser Glu
        555                 560

ATA TAT CCA GAT TTC GTG ACG ATC GCC AAA GGG TTC                1764
Ile Tyr Pro Asp Phe Val Thr Ile Ala Lys Gly Phe
565                 570                 575

AAC ATT CCA GCG GTC CGT GTG ACA AAG AAG AAC GAA                1800
Asn Ile Pro Ala Val Arg Val Thr Lys Lys Asn Glu
            580                 585

GTC CGC GCA GCG ATA AAG AAG ATG CTC GAG ACT CCA                1836
Val Arg Ala Ala Ile Lys Lys Met Leu Glu Thr Pro
    590                 595                 600

GGG CCG TAC CTC TTG GAT ATA ATC GTC CCA CAC CAG                1872
Gly Pro Tyr Leu Leu Asp Ile Ile Val Pro His Gln
                605                 610

GAG CAT GTG TTG CCT ATG ATC CCT AGT GGT GGG GCT                1908
Glu His Val Leu Pro Met Ile Pro Ser Gly Gly Ala
        615                 620

TTC AAG GAT ATG ATC CTG GAT GGT GAT GGC AGG ACT                1944
Phe Lys Asp Met Ile Leu Asp Gly Asp Gly Arg Thr
625                 630                 635

GTG TAC                                                        1950
Val Tyr
    638

TGATCTAAAA TCCAGCAAG                                           1969
```

IMIDAZOLINONE RESISTANT AHAS MUTANTS

This is a continuation of application Ser. No. 07/894,062, filed Jun. 8, 1992 now U.S. Pat. No. 5,767,361. Each of these prior applications is hereby incorporated herein by reference, in its entirety which is continuation-in-part of Ser. No. 07/737,851 filed Jul. 31, 1991 now U.S. Pat. No. 5,731,180.

This invention relates to novel DNA sequences that encode novel variant forms of acetohydroxy acid synthase enzyme (hereinafter AHAS). The AHAS enzyme is a critical enzyme routinely produced in a variety of plants and a broad range of microorganisms. Normal AHAS function is inhibited by imidazolinone herbicides; however, new AHAS enzymes encoded by the mutant DNA sequences function normally catalytically even in the presence of imidazolinone herbicides and, therefore, confer herbicide resistance upon the plant or microorganism containing them.

The novel DNA sequences are derived from corn and have a substitution of an amino acid at position 621 of the normal AHAS sequence. This substitution in the AHAS gene sequence results in a fully functional enzyme, but renders the enzyme specifically resistant to inhibition by a variety of imidazolinone herbicides. The availability of these variant sequences provides a tool for transformation of different crop plants to imidazolinone herbicide resistance, as well as providing novel selectable markers for use in other types of genetic transformation experiments.

BACKGROUND OF THE INVENTION

The use of herbicides in agriculture is now widespread. Although there are a large number of available compounds which effectively destroy weeds, not all herbicides are capable of selectively targeting the undersirable plants over crop plants, as well as being non-toxic to animals. Often, it is necessary to settle for compounds which are simply less toxic to crop plants than to weeds. In order to overcome this problem, development of herbicide resistant crop plants has become a major focus of agricultural research.

An important aspect of development of herbicide-resistance is an understanding of the herbicide target, and then manipulating the affected biochemical pathway in the crop plant so that the inhibitory effect is avoided while the plant retains normal biological function. One of the first discoveries of the biochemical mechanism of herbicides related to a series of structurally unrelated herbicide compounds, the imidazolinones, the sulfonylureas and the triazolopyrimidines. It is now known (Shaner et al. *Plant Physiol.* 76: 545–546,1984; U.S. Pat. No. 4,761,373) that each of these herbicides inhibits plant growth by interference with an essential enzyme required for plant growth, acetohydroxyacid synthase (AHAS; also referred to as acetolacetate synthase, or ALS). AHAS is required for the synthesis of the amino acids isoleucine, leucine and valine.

The AHAS enzyme is known to be present throughout higher plants, as well as being found in a variety of microorganisms, such as the yeast *Saccharomyces cerevisiae*, and the enteric bacteria, *Escherichia coli* and *Salmonella typhimurium*. The genetic basis for the production of normal AHAS in a number of these species has also been well characterized. For example, in both *E. coli* and *S. typhimurium* three isozymes of AHAS exist; two of these are sensitive to herbicides while a third is not. Each of these isozymes possesses one large and one small protein subunit; and map to the IlvIH, IlvGM and IlvBN operons. In yeast, the single AHAS isozyme has been mapped to the ILV2 locus. In each case, sensitive and resistant forms have been identified and sequences of the various alleles have been determined (Friden et. al., *Nucl. Acid Res.* 13: 3979–3993, 1985; Lawther et al., *PNAS USA* 78: 922–928, 1982; Squires et al., *Nucl. Acids Res* 811: 5299–5313, 1983; Wek et al; *Nucl. Acids Res* 13: 4011–4027, 1985; Falco and Dumas, *Genetics* 109, 21–35, 985; Falco et al, *Nucl. Acids Res* 13; 4011–4027, 1985).

In tobacco, AHAS function is encoded by two unlinked genes, SuRA and SuRB. There is substantial identity between the two genes, both at the nucleotide level and amino acid level in the mature protein, although the N-terminal, putative transit region differs more substantially (Lee et al, *EMBO J.* 7: 1241–1248, 1988). Arabidopsis, on the other hand, has a single AHAS gene, which has also been completely sequenced (Mazur et al., *Plant Physiol.* 85:1110–1117, 1987). Comparisons among sequences of the AHAS genes in higher plants indicates a high level of conservation of certain regions of the sequence; specifically, there are at least 10 regions of sequence conservation. It has previously been assumed that these conserved regions are critical to the function of the enzyme, and that retention of that function is dependent upon substantial sequence conservation.

It has been recently reported (U.S. Pat. No. 5,013,659) that mutants exhibiting herbicide resistance possess mutations in at least one amino acid in one or more of these conserved regions. In particular, substitution of certain amino acids for the wild type amino acid at these specific sites in the AHAS protein sequence have been shown to be tolerated, and indeed result in herbicide resistance of the plant possessing this mutation, while retaining catalytic function. The mutations described therein encode either cross resistance for imidazolinones and sulfonylureas or sulfonylurea-specific resistance, but no imidazolinone-specific mutations were disclosed. These mutations have been shown to occur at both the SuRA and SuRB loci in tobacco; similar mutations have been isolated in Arabidopsis and yeast.

Imidazolinone-specific resistance has been reported elsewhere in a number of plants. U.S. Pat. No. 4,761,373 generally described an altered AHAS as a basis of herbicide resistance in plants, and specifically disclosed certain imidazolinone resistant corn lines. Haughn et al. (*Mol. Gen. Genet.* 211:266–271, 1988) disclosed the occurrence of a similar phenotype in Arabidopsis. Sathasivan et al. (Nucl. Acid Res. 18:2188, 1990) identified the imidazolinone-specific resistance in Arabidopsis as being based on a mutation at position 653 in the normal AHAS sequence. In accordance with the present invention, a gene encoding imidazolinone-specific resistance in a monocot has now been isolated and determined to be associated with a single amino acid substitution in a wild-type monocot AHAS amino acid sequence.

SUMMARY OF THE INVENTION

The present invention provides novel nucleic acid sequences encoding functional monocot AHAS enzymes insensitive to imidazolinone herbicides. The sequences in question comprise a mutation in the codon encoding the amino acid serine at position 621 in the corn (maize) AHAS sequence, or in the corresponding position in other monocot sequences. Other monocots, such as wheat, are also known to exhibit imidazolinone specific mutations (e.g., ATCC Nos. 40994–97). In corn, the wild type sequence has a serine at this position. In a preferred embodiment, the substitution is asparagine for serine, but alternate substitutions for serine include aspartic acid, glutamic acid, glutamine and tryptophane. Although the claimed sequences are originally derived from monocots, the novel sequences are useful in methods for producing imidazolinone resistant cells in any type of plant, said methods comprising transforming a target plant cell with one or more of the altered sequences provided herein. Alternatively, mutagenesis is utilized to create mutants in plant cells or seeds containing a nucleic acid sequence encoding an imidazolinone insensitive AHAS. In the case of mutant plant cells isolated in tissue culture, plants which possess the imidazolinone resistant or insensitive trait are then regenerated. The invention thus also encompasses plant cells, bacterial cells, fungal cells, plant tissue cultures, adult plants, and plant seeds that possess a mutant nucleic acid sequence and which express functional imidazolinone resistant AHAS enzymes.

The availability of these novel herbicide resistant plants enables new methods of growing crop plants in the presence of imidazolinones. Instead of growing non-resistant plants, fields may be planted with the resistant plants produced by mutation or by transformation with the mutant sequences of the present invention, and the field routinely treated with imidazolinones, with no resulting damage to crop plants.

The mutant nucleic acids of the present invention also provide novel selectable markers for use in transformation experiments. The nucleic acid sequence encoding a resistant AHAS is linked to a second gene prior to transfer to a host cell, and the entire construct transformed into the host. Putative transformed cells are then grown in culture in the presence of inhibitory amounts of herbicide; surviving cells will have a high probability of having successfully acquired the second gene of interest. Alternately, the resistant AHAS gene can be cotransformed on an independent plasmid with the gene of interest, whereby about 50% of all transformants can be expected to have received both genes.

The following definitions should be understood to apply throughout the specification and claims. A "functional" or "normal" AHAS enzyme is one which is capable of catalyzing the first step in the pathway for synthesis of the essential amino acids isoleucine, leucine and valine. A "wild-type" AHAS sequence is a sequence present in an imidazolinone sensitive member of a given species. A "resistant" plant is one which produces a mutant but functional AHAS enzyme, and which is capable of reaching maturity when grown in the presence of normally inhibitory levels of imidazolinone. The term "resistant", as used herein, is also intended to encompass "tolerant" plants, i.e., those plants which phenotypically evidence adverse, but not lethal, reactions to the imidazolinone.

BRIEF DESCRIPTION OF THE FIGURES

FIG. 6: Nucleotide and deduced amino acid sequences of the XI12/8A mutant AHAS gene.

FIG. 7: Nucleotide sequence alignment of XI12/8A, B73/7-4 and W22/1A als2 genes. (*) marks the base change causing the mutation at position 621, (#) differences from the B73/7-4 sequence and (>) represents silent changes.

FIG. 8: Amino acid sequences and alignment of XI12/BA, B73/7-4 and W22/1A als2 genes. (*) marks the mutation at position 621, (#) marks differences from the B73/7-4 sequence, and (>) represents silent changes.

DETAILED DESCRIPTION OF THE INVENTION

The gene of the present invention is isolatable from corn maize line XI12 (seed deposited with the American Type Culture Collection as Accession Number 75051), and has been inserted into plasmid pXI12/8A (deposited with the American Type Culture Collection as Accession Number 68643). It is also isolatable from any other imidazolinone-specific herbicide resistant mutant, such as the corn line QJ22 (deposited as a cell culture with the American Type Culture Collection as Accession Number 40129), or the various wheat plants (seed deposited with the American Type Collection as Accession Numbers 40994, 40995, 40996, or 40997). A genomic DNA library is created, for example, in phage EMBL-3 with DNA from one of the imidazolinone resistant mutants, preferably one which is homozygous for the resistance trait, and is screened with a nucleic acid probe comprising all or a part of a wild-type AHAS sequence.

In maize, the AHAS gene is found at two loci, als1 and als2 (Burr and Burr, Trends in Genetics 7:55–61, 1991); the homology between the two loci is 95% at the nucleotide level. The mutation in XI12 is mapped to locus als2 on chromosome 5, whereas the nonmutant gene is mapped to locus als1 on chromosome 4 (Newhouse et al., "Imidazolinone-resistant crops". *In The Imidazolinone Herbicides*, Shaner and O'Connor (Eds.), CRC Press, Boca Raton, Fla., in Press) Southern analysis identifies some clones containing the mutant als2 gene, and some containing the non-mutant als1 gene. Both types are subcloned into sequencing vectors, and sequenced by the dideoxy sequencing method.

Figures 4, 5B:
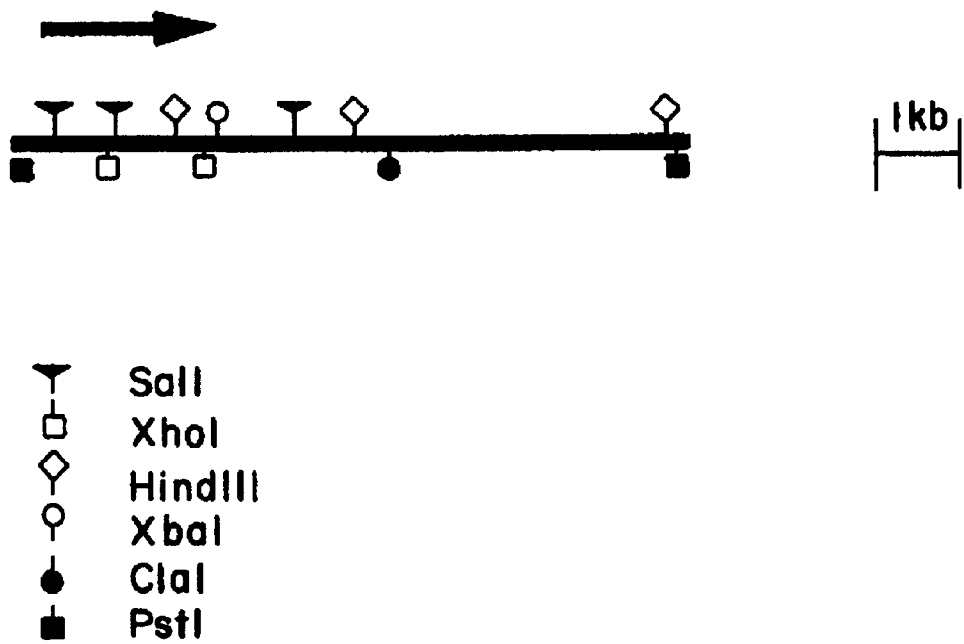
FIG. 4: Restriction map of plasmid pCD8A. The mutant AHAS gene from XI12 was subcloned as a 8 kb Pstl fragment into vector pKS(+). The location and orientation of the AHAS gene is indicated by an arrow. The restriction sites of Pstl, Xhol, HindIII, XbaI and ClaI are represented by symbols.
Figure 5A:
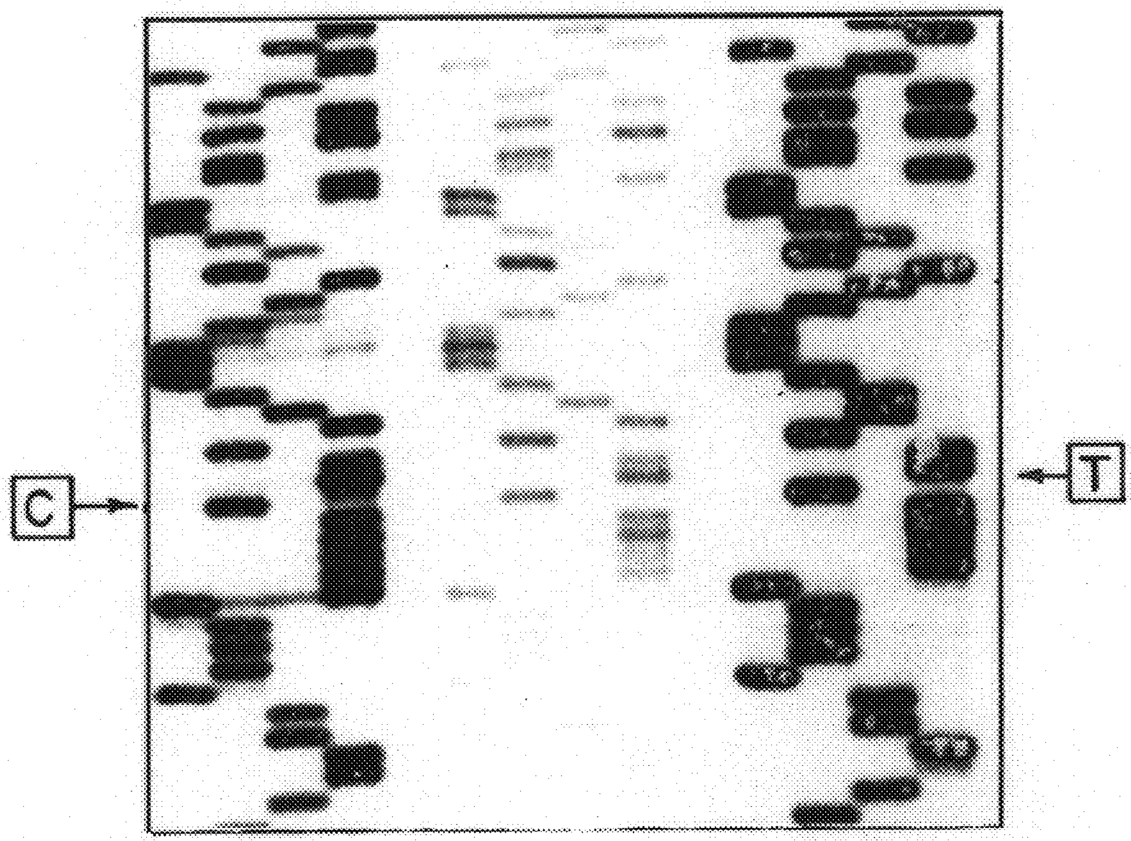
FIG. 5: Nucleotide sequencing gel of the non-coding strand (A) and the double stranded DNA sequence (B) of AHAS clones W22/4-4, B73/10-4 and XI12/8A in the region of amino acids 614 to 633. The position of the cytosine to thymidine transition is indicated by an arrow.

Sequencing and comparison of wild type and mutant AHAS genes shows a difference of a single nucleotide in the codon encoding the amino acid at position 621 (FIG. 5). Specifically, the codon AGT encoding serine in the wild type is changed to AAT encoding asparagine in the mutant AHAS (FIG. 8). The mutant AHAS gene is otherwise similar to the wild type gene, encoding a protein having 638 amino acids, the first 40 of which constitute a transit peptide which is thought to be cleaved during transport into the chloroplast in vivo. The sequence of the als1 non-mutant gene from XI12 appears to be identical to the als1 gene from B73.

The mutant genes of the present invention confer resistance to imidazolinone herbicides, but not to sulfonylurea herbicides. Types of herbicides to which resistance is conferred are described for example in U.S. Pat. Nos. 4,188,487; 4,201,565; 4,221,586; 4,297,128; 4,554,013; 4,608,079; 4,638,068; 4,747,301; 4,650,514; 4,698,092; 4,701,208; 4,709,036; 4,752,323; 4,772,311; and 4,798,619.

It will be understood by those skilled in the art that the nucleic acid sequence depicted in FIG. 6 is not the only sequence which can be used to confer imidazolinone-specific resistance. Also contemplated are those nucleic acid sequences which encode an identical protein but which, because of the degeneracy of the genetic code, possess a different nucleotide sequence. The invention also encompasses genes encoding AHAS sequences in which the aforestated mutation is present, but which also encode one or more silent amino acid changes in portions of the molecule not involved with resistance or catalytic function. Also contemplated are gene sequences from other imidazolinone resistant monocots which have a mutation in the corresponding region of the sequences.

For example, alterations in the gene sequence which result in the production of a chemically equivalent amino acid at a given site are contemplated; thus, a codon for the amino acid alanine, a hydrophobic amino acid, can readily be substituted by a codon encoding another hydrophobic residue, such as glycine, or may be substituted with a more hydrophobic residue such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product. The invention also encompasses chimaeric genes, in which the substituted portion of the corn AHAS gene is recombined with unaltered portions of the normal AHAS genes from other species. Thus, throughout the specification and claims, wherever the term "imidazolinone-specific resistant corn AHAS gene" is used, it is intended to cover each of these alternate embodiments as well as the sequence of FIG. 6.

Isolated AHAS DNA sequences of the present invention are useful to transform target crop plants, and thereby confer imidazolinone resistance. A broad range of techniques currently exist for achieving direct or indirect transformation of higher plants with exogenous DNA, and any method by which the novel sequence can be incorporated into the host genome, and stably inherited by its progeny, is contemplated by the present invention. The imidazolinone specific resistance trait is inherited as a single dominant nuclear gene. The level of imidazolinone resistance is increased when the gene is present in a homozygous state; such corn plants, for example, have a resistance level of about 1,000 times that of a non-resistant plant. Plants heterozygous for the trait, however, have a resistance of about 50–500 times that of a non-resistant plant.

Transformation of plant cells can be mediated by the use of vectors. A common method of achieving transformation is the use of *Agrobacterium tumefaciens* to introduce a foreign gene into the target plant cell. For example, the mutant AHAS sequence is inserted into a plasmid vector containing the flanking sequences in the Ti-plasmid T-DNA. The plasmid is then transformed into *E. coli*. A triparental mating among this strain, an Agrobacterium strain containing a disarmed Ti-plasmid containing the virulence functions needed to effect transfer of the AHAS containing T-DNA sequences into the target plant chromosome, and a second *E. coli* strain containing a plasmid having sequences necessary to mobilize transfer of the AHAS construct from *E. coli* to Agrobacterium is carried out. A recombinant Agrobacterium strain, containing the necessary sequences for plant transformation is used to infect leaf discs. Discs are grown on selection media and successfully transformed regenerants are identified. The recovered plants are resistant to the effects of herbicide when grown in its presence. Plant viruses also provide a possible means for transfer of exogenous DNA.

Direct uptake of plant cells can also be employed. Typically, protoplasts of the target plant are placed in culture in the presence of the DNA to be transferred, and an agent which promotes the uptake of DNA by protoplast. Useful agents in this regard are polyethylene glycol or calcium phosphate.

Alternatively, DNA uptake can be stimulated by electroporation. In this method, an electrical pulse is used to open temporary pores in a protoplast cell membrane, and DNA in the surrounding solution is then drawn into the cell through the pores. Similarly, microinjection can be employed to deliver the DNA directly into a cell, and preferably directly into the nucleus of the cell.

In each of the foregoing techniques, transformation occurs in a plant cell in culture. Subsequent to the transformation event, plant cells must be regenerated to whole plants. Techniques for the regeneration of mature plants from callus or protoplast culture are now well known for a large number of different species (see, e.g., *Handbook of Plant Cell Culture*, Vols. 1–5, 1983–1989 McMillan, N.Y.) Thus, once transformation has been achieved, it is within the knowledge in the art to regenerate mature plants from the transformed plant cells.

Alternate methods are also now available which do not necessarily require the use of isolated cells, and therefore, plant regeneration techniques, to achieve transformation. These are generally referred to as "ballistic" or "particle acceleration" methods, in which DNA coated metal particles are propelled into plant cells by either a gunpowder charge (Klein et al., *Nature* 327: 70–73, 1987) or electrical discharge (EPO 270 356). In this manner, plant cells in culture or plant reproductive organs or cells, e.g. pollen, can be stably transformed with the DNA sequence of interest.

In certain dicots and monocots direct uptake of DNA is the preferred method of transformation. For example, in corn, the cell wall of cultured cells is digested in a buffer with one or more cell wall degrading enzymes, such as cellulase, hemicellulase and pectinase, to isolate viable protoplasts. The protoplasts are washed several times to remove the enzymes, and mixed with a plasmid vector containing the gene of interest. The cells can be transformed with either PEG (e.g. 20% PEG 4000) or by electroporation. The protoplasts are placed on a nitrocellulose filter and cultured on a medium with embedded corn cells functioning as feeder cultures. After 2–4 weeks, the cultures in the nitrocellulose filter are placed on a medium containing about 0.32 $\mu$M of the imidazolinone and maintained in the medium for 1–2 months. The nitrocellulose filters with the plant cells are transferred to fresh medium with herbicides and nurse cells every two weeks. The untransformed cells cease growing and die after a few weeks.

The present invention can be applied to transformation of virtually any type of plant, both monocot and dicot. Among the crop plants for which transformation to herbicide resistance is contemplated are corn, wheat, rice, millet, oat, barley, sorghum, sunflower, sweet potato, alfalfa, sugar beet, Brassica species, tomato, pepper, soybean, tobacco, melon, squash, potato, peanut, pea, cotton, or cacao. The novel sequences may also be used to transform ornamental species, such as rose, and woody species, such as pine and poplar.

The novel sequences of the invention also are useful as selectable markers in plant genetics studies. For example, in plant transformation, sequences encoding imidazolinone resistance could be linked to a gene of interest which is to be used to transform a target imidazolinone sensitive plant cell. The construct comprising both the gene of interest and the imidazolinone resistant sequence are introduced into the plant cell, and the plant cells are then grown in the presence of an inhibitory amount of an imidazolinone. Alternately, the second gene of interest can be cotransformed, on a separate plasmid, into the host cells. Plant cells surviving such treatment presumably have acquired the resistance gene as well as the gene of interest, and therefore, only transformants survive the selection process with the herbicide. Confirmation of successful transformation and expression of both genes can be achieved by Southern hybridization of genomic DNA, by PCR or by observation of the phenotypic expression of the genes.

The invention is further illustrated by the following non-limiting examples.

EXAMPLES

1. Confirmation of Whole Plant Herbicide Resistance in XI12

XI12 plants are treated with herbicides at 10 days to the V3 leaf stage (4–5 leaves, of which 3 have visible ligules). Imazethapyr is applied at rates of 2000, 500, 250, 125 and 62.5 g/ha. Chlorsulfuron is applied at 32, 16, 8, 4 and 2 g/ha. Plants are treated postemergence at a spray volume of 400 l/ha. After spraying, plants are placed in the greenhouse for further observation.

XI12 plants are unaffected at all rates of imazethapyr treatment; however, no visible increased resistance to chlorsulfuron is noted. Thus, XI12 displays selective resistance to the imidazolinone at the whole plant level (See FIG. 1).

The resistance in XI12 is also shown to be inherited as a single dominant allele of a nuclear gene. Heterozygous resistant XI12 are selfed, and the selfed progeny segregate in the 3 resistant:1 susceptible ratio expected for a single dominant allele of a nuclear gene. In this study, the segregating seedlings are sprayed postemergence with lethal doses of imazethapyr (125 or 250 g/ha) following spraying protocols described above, to establish segregation for resistance.

2. AHAS Extraction

Seeds of XI12 are sown in soil in a green-house maintained at day/night temperature of 80° C. and 15 hour photoperiod. Plants are harvested two weeks after planting. The basal portion of the shoot is used for the extraction of AHAS. 5 g of the tissue are powdered in liquid nitrogen and then homogenized in AHAS assay buffer comprising 100 mM potassium phosphate buffer (pH 7.5) containing 10 mM pyruvate, 5 mM $MgCl_2$, 5 mM EDTA, 100 uM FAD (flavin adenine dinucleotide), 1 mM valine, 1 mM leucine, 10% glycerol and 10 mM cysteine. The homogenate is centrifuged at 10,000 rpm for 10 minutes and 3 ml of the supernatant are applied onto an equilibrated Bio-Rad Econo-Desalting column (10 DG) and eluted with 4 ml AHAS assay buffer.

AHAS activity is measured by estimation of the product, acetolactate, after conversion by decarboxylation in the presence of acid to acetoin. Standard reaction mixtures contain the enzyme in 50 mM potassium phosphate (pH 7.0) containing 100 mM sodium pyruvate, 10 mM $MgCl_2$, 1 mM thiamine pyrophosphate, 10 uM FAD, and appropriate concentrations of different inhibitors. This mixture is incubated at 37° C. for 1 to 3 hours depending upon the experiment. At the end of this incubation period, the reaction is stopped with the addition of $H_2SO_4$ to make a final concentration of 0.85% $H_2SO_4$ in the tube. The reaction product is allowed to decarboxylate at 60° C. for 15 minutes. The acetoin formed is determined by incubating with creatine (0.17%) and 1-naphthol (1.7% in 4N NaOH). The absorption of color complex formed is measured at 520 nm.

Figure 1A:
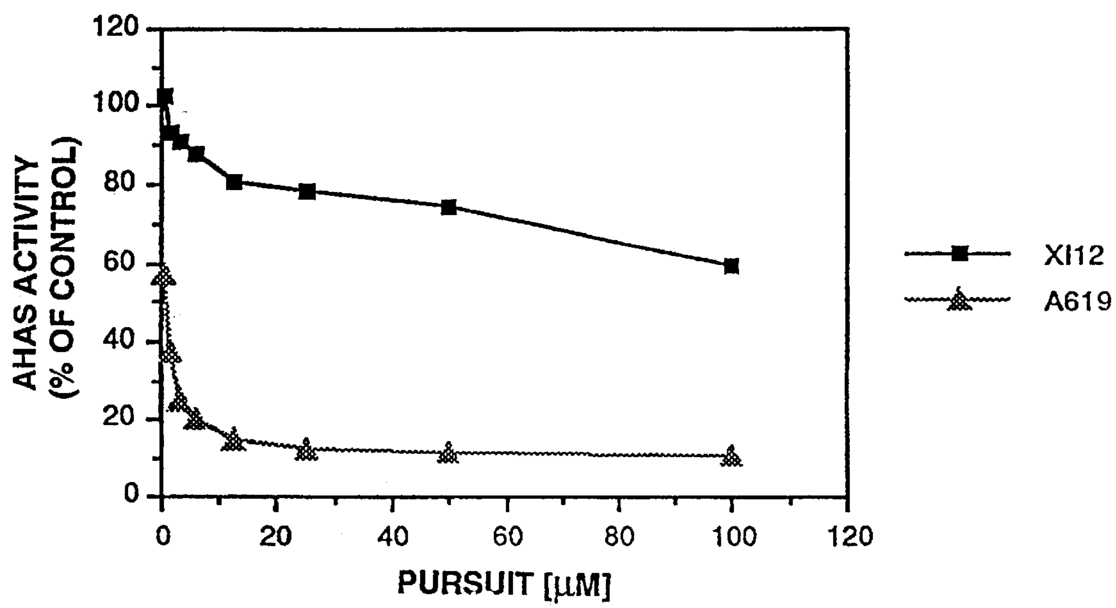
FIG. 1: AHAS enzyme activity in 10-day old maize seedlings (corn lines A619 or XI12) in the presence of imazethapyr (Pursuits™ A) or chlorsulfuron (Oust™ B). Herbicide resistant AHAS activity is calculated as percentage of AHAS activity in the absence of inhibitor. The standard error between experimets is 10%.
Figure 1B:
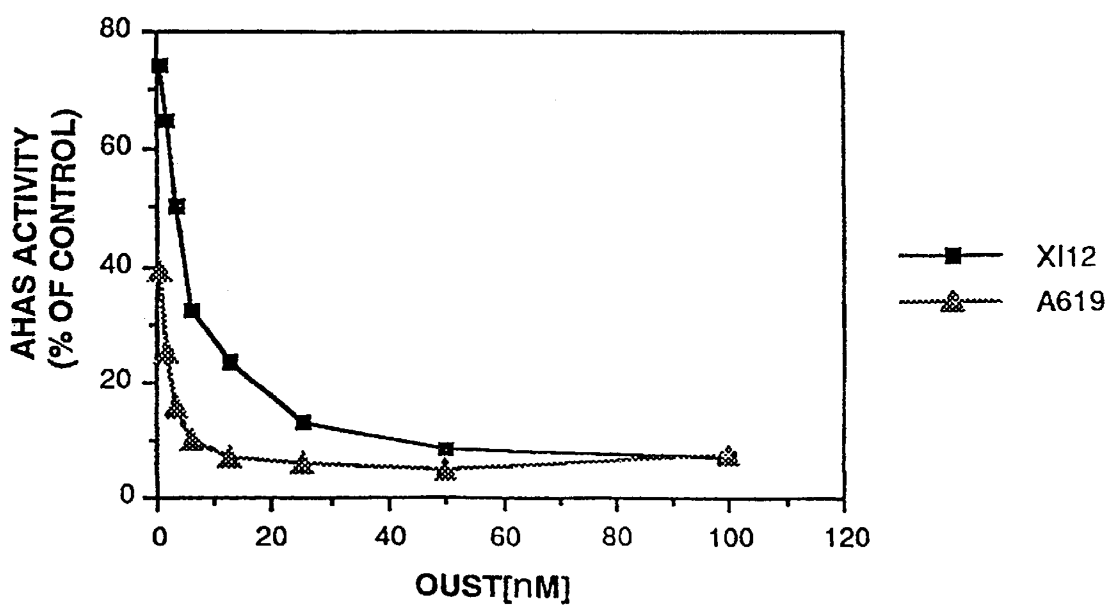

AHAS activity from B73, A619, or other wild-type maize lines is highly sensitive to inhibition by imazethapyr (PURSUIT™) with an $I_{50}$ of 1 uM (See FIG. 1). Contrary to this observation, XI12 shows 70–80% of enzyme activity at the highest concentrations (100 $\mu$M) of PURSUIT™ or ARSENAL™ (imazepyr), and about 70% in the presence of SCEPTERS™ (imazequin). This result shows a 100-fold increase in tolerance of AHAS activity from XI12 to imazethapyr as compared to the in vitro AHAS activity from A619. Sensitivity of AHAS activity from the two lines to sulfonylureas gives a different picture. In the presence of OUST™ (sulfometuron methyl), at 100 nM, AHAS activity of XI12 is only 15–20%. AHAS activity of A619 in the presence of OUST™ IS 5–10%, and in the presence of PURSUIT™ is 15–20% (See FIG. 1).

3. Cloning of XI12 AHAS Genes

Seeds of the XI12 mutant derived from an imidazolinone resistant corn tissue culture line are planted; plants obtained therefrom appear to be segregating for the mutant AHAS phenotype. In order to obtain homozygous resistant seed material, a population of XI12 mutant plants are selfed. After selecting for herbicide resistance for three consecutive growing seasons, the seeds are homozygous for the mutant AHAS gene. Homozygous seeds are collected and used to grow seedlings to be used in AHAS gene isolation.

DNA is extracted from 7 days old etiolated seedlings of a homozygous XI12 line. 60 g of plant tissue is powdered in liquid nitrogen, and transfered into 108 ml DNA extraction buffer (1.4 M NaCl, 2.0% Ctab (hexadecyl trimethyl ammonium bromide), 100 mM tris-Cl pH 8.0, 20 mM EDTA, 2% Mercaptoethanol) and 54 ml water. After incubation at 50–60° C. for 30 minutes the suspension is extracted with an equal amount of chloroform. The DNA is precipitated by adding an equal amount of precipitation buffer (1% Ctab, 50 mM Tris-Cl pH 8.0, 10 mM EDTA). To purify the genomic DNA, a high speed centrifugation in 6.6M CsCl and ethidium bromide is performed (Ti80 rotor, 50,000 rpm, 20° C., 24 hours). The purified DNA is extracted with salt saturated Butanol and dialyzed for 25 hours against 3 changes of 1 l dialysis buffer (10 mM Tris-Cl Ph 8.0, 1 mM EDTA, 0.1M NaCl). The concentration of the XI12 genomic DNA is determined spectrophotometrically to be 310 mg/ml. The yield is 0.93 mg.

The XI12 genomic DNA is used to create a genomic library in the phage EMBL-3. The DNA is partially digested with Mbol and the fragments are separated on a sucrose gradient to produce size range between 8 to 22 kb before cloning into the BamHl site of EMBL-3. After obtaining $2.1\times10^6$ independent clones, the library is amplified once. The titer of the library is determined $9\times10^{10}$ pfu/ml.

To obtain probes for analysis of the XI12 library, a W22 (wild-type) cDNA library in lambda gt11, purchased from Clontech Inc., CA, is screened with an 800 nt BamH1 probe isolated from Arabidopsis AHAS genomic clone. The phages are plated in a density of 50,000 pfu/15 cm plate, transferred onto nitrocellulose filters, prehybridized in 6× SSC, 0.2% SDS for 2 hours and hybridized with the Arabidopsis AHAS probe in 6× SSC, 0.2% SDS overnight. One positive phage is identified, further purified and used for subcloning of a 1.1 kb EcoRl fragment. The 1.1 kb EcoRl fragment is subcloned into pGemA-4 and used as a probe to identify the XI12 AHAS genes.

Figure 2B:
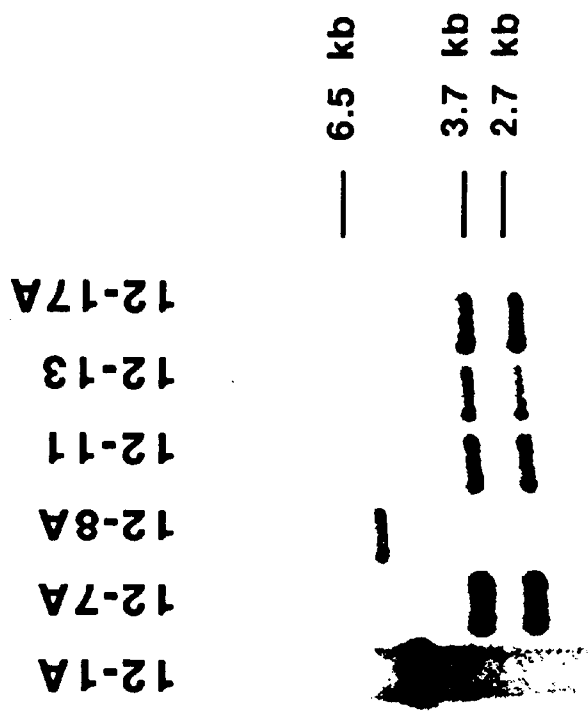
FIG. 2: Southern analysis of genomic clones in phage EMBL3. Phages 12-1A (from W22), 12-7A, 18-8A, 12-11, and 12-17A (From XI12) are digested with Xbal or Sall, separated on a 1% agarose gel, transfered onto nitrocellulose and hybridized with an AHAS cDNA fragment as probe.
Figure 2A:
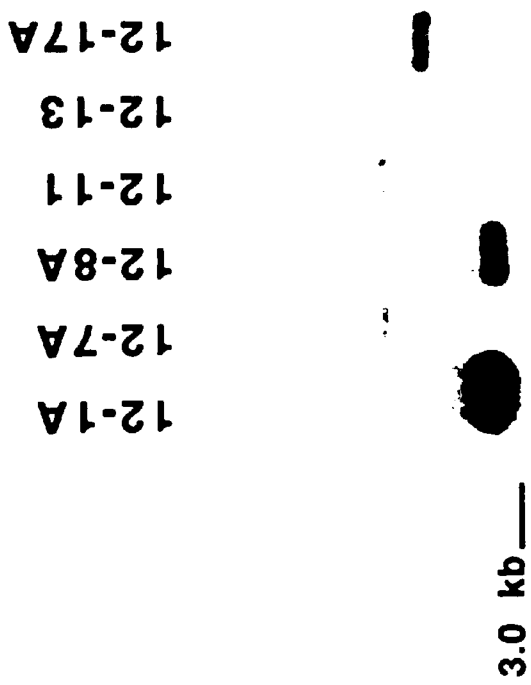
Figure 3:
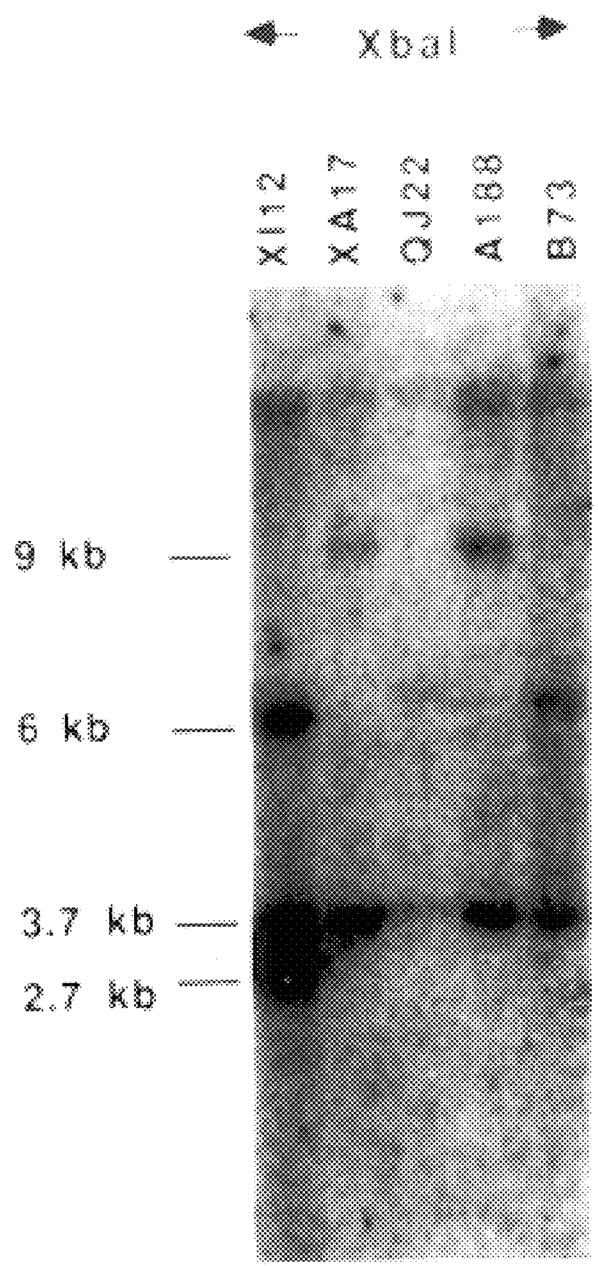
FIG. 3: Southern analysis of genomic DNA from corn lines XI12, XA17, QJ22, A188 and B73. The DNA is digested with Xbal, separated on a 1% agarose gel, transferred onto nitrocellulose and hybridized with an AHAS cDNA fragment as probe.

The X112 genomic library is plated on 12 15-cm plates (concentration of 50,000 pfu/plate) and is screened with the W22 AHAS cDNA probe. The filters are prehybridized (2 hours) and hybridized (over night) in Church buffer (0.5 M Na Phosphate, 1 mM EDTA, 1% BSA, 7% SDS) at 65° C. and washed at 65° C. in 2× SSC, 0.2% SDS and 0.3× SSC, 0.2% SDS. 12 positive plaques are obtained from a total of $7.5 \times 10^5$ pfu screened and 5 positive clones are further purified and isolated according to Chisholm (BioTechniques 7:21–23, 1989). Southern analysis (See FIG. 2) showed that the phage clones represented two types of AHAS clones: Type-1 clones contain one large Xbal (>6.5 kb) fragment hybridizing to the AHAS cDNA probe, Type-2 clones contained two 2.7 and 3.7 kb Xbal fragments hybridizing to the AHAS cDNA probe. Genomic Southern of XI12 DNA demonstrated, that the Xbal fragments obtained by digesting genomic DNA and by hybridizing to the AHAS cDNA probe correspond to the Xbal fragments identified in the XI12 phage clones (see FIG. 3). Restriction digest and Southern Analysis also demonstrate that of the 5 AHAS clones, one clone represents the mutant als2 genes and four represent the als1 gene.

The AHAS genes corresponding to the mutant locus located on chromosome 5 (clone 12/8A) and the non-mutant locus located on chromosome 4 (clone 12/17A) are subcloned as a Pstl fragment (clone 12/8A) or as Xbal fragment (12/17A) into the sequencing vector pBluescript II KSm13 (+) (pKS+; Stratagene). Both 2.7 kb and 3.7 kb XbaI fragments from phage 12/17A contain one complete copy of AHAS genes which are identified. The sequence of each is obtained by dideoxy sequencing (Pharmacia T7 sequencing Kits) using primers complementary to the AHAS coding sequence.

The methods of DNA extraction, cloning of the genomic library and screening of the library are as described for the XI12 genomic DNA. The B73 AHAS genes are subcloned into the sequencing vector pKS+ as Xbal fragments and are sequenced. The sequence is obtained by dideoxy sequencing, using primers complementary to the AHAS coding sequence as described for the SI12 AHAS genes.

A W22 genomic library in EMBL3 purchased from Clontech Inc., CA is screened. The phages are plated in a density of 50,000 pfu/7 inch plate, transferred onto nitrocellulose filters, and hybridized with the W22 AHAS cDNA probe described above (prehybridization and hybridization conditions: 6× SSC, 0.5% SDS, 1× Denhard's 100 mg/ml calf thymus DNA, 65° C., washing conditions: 3X× SSC, 0.2% SDS for 2 hours at 65° C., and 0.3× SSC, 0.2% SDS for 2 hours). Two positive phages (12/1A and 12/4-4) are identified and further purified.

The W22 genomic clone 12/1A is subcloned as two 0.78 kb (pGemA-4) and 3.0 kb (pGemA-14; Promega) Sall fragments into the vector pGem-A2, and as a 6.5 kb Xbal fragment into the vector pKS+ (pCD200). The coding strand sequence of the W22 AHAS gene is obtained by dideoxy sequencing of nested deletions created from subclones pGem A-14 and pGem A-4 of phage 12-1A. This sequence is used to design oligonucleotides complementary to the AHAS non-coding strand. The sequence of the non-coding strand is obtained by dideoxy sequencing of clone pCD200 using primers complementary to the coding strand. Upon complementing the sequencing of the W22 AHAS gene, primers of both DNA strands are designed and used for the sequencing of the AHAS genes isolated from the XI12 and B73 genomic libraries.

4. Cloning of QJ22 AHAS Genes

The sequence of the gene encoding AHAS in the maize line QJ22, which is selectively resistant to imidazolinones, is also determined. A genomic library of QJ22 is prepared in an EMBL3 vector. A library of 800,000 phage is screened with an 850 nucleotide SalI/ClaI fragment isolated from an AHAS clone (A-4) derived from the wild-type maize line W22. Five positive phages are picked and submitted to a second round of screening to partially purify the phage. The partially purified phage are analyzed by PCR to determine if any clones represent the QJ22 als1 gene. Such clones are identified as a 3.7 kb XbaI fragment with a gene specific SmaI site at position 495. The second screen indicates the presence of a single positive clone with these characteristics.

The PCR product is purified using a commercial kit (Magic PCR Preps) from Promega, and the purified DNA is sequenced with a Taq polymerase sequencing system "fmol", also from Promega Sequence analysis of both strands of the DNA of the QJ22 mutant AHAS shows a nucleotide transition from G to A in the codon for amino acid 621. This mutation is identical to the one seen in XI12 and the remainder of the sequence is typical of an als1gene.

Results

The sequence of the mutant AHAS genes is compared with the sequences obtained from the wild type corn lines B73 and W22 (See FIG. 7). The XI12 mutant gene (XI12/8A) and the wild type gene are identical except for the amino acid change at position 621, causing a single nucleotide transition from AGT to AAT (See FIG. 8). The XI12 mutant XI12/8A and the wild-type B73/7-4 gene show an additional difference at position 63. On the other hand, the non-mutant XI12 AHAS gene cloned in XI12/17A is completely homologous to the corresponding B73/10-2 in the region coding for the mature AHAS protein (data not shown).

Deposit of Biological Materials

The following biological materials were deposited with the American Type Culture Collection, 10801 University Blvd., Manassas, Va., as follows:

*E. coli* XLI Blue harboring plasmid pX12/8A, deposited on Jul. 3, 1991, Accession Number ATCC 68643

XI12 corn seed deposited on Jul. 16, 1991, Accession Number ATCC 75051.

What we claim is:

1. An isolated functional corn AHAS enzyme which has an amino acid substitution at position 621 relative to the wild-type corn AHAS enzyme, which substitution confers imidazoline-specific resistance to the enzyme.

2. The enzyme of claim 1 in which the substituted amino acid is asparagine.

3. A method of selecting host cells successfully transformed with a gene of interest which comprises providing to prospective host cells the gene of interest linked to a polynucleotide which encodes the corn AHAS enzyme of claim 1, or providing said gene unlinked but in the presence of said polynucleotide, growing the cells in the presence of an inhibitory amount of imidazolinone and identifying surviving cells as containing the gene of interest.

* * * * *